(12) United States Patent
Jacobson et al.

(10) Patent No.: US 10,273,471 B2
(45) Date of Patent: Apr. 30, 2019

(54) COMPOSITIONS AND METHODS FOR MULTIPLEX NUCLEIC ACIDS SYNTHESIS

(71) Applicant: Gen9, Inc., Cambridge, MA (US)

(72) Inventors: Joseph Jacobson, Newton, MA (US); Daniel Schindler, Newton, MA (US); Ishtiaq Saaem, Dhaka (BD); Scott Lawton, Bedford, MA (US); Martin J. Goldberg, Saratoga, CA (US); Michael E. Hudson, Framingham, MA (US); Li-yun A. Kung, Arlington, MA (US)

(73) Assignee: Gen 9, Inc., Cambridge, MA (US)

( * ) Notice: Subject to any disclaimer, the term of this patent is extended or adjusted under 35 U.S.C. 154(b) by 240 days.

(21) Appl. No.: 14/766,195

(22) PCT Filed: Mar. 13, 2014

(86) PCT No.: PCT/US2014/026261
§ 371 (c)(1),
(2) Date: Aug. 6, 2015

(87) PCT Pub. No.: WO2014/151696
PCT Pub. Date: Sep. 25, 2014

(65) Prior Publication Data
US 2015/0376602 A1 Dec. 31, 2015

Related U.S. Application Data

(60) Provisional application No. 61/792,245, filed on Mar. 15, 2013.

(51) Int. Cl.
*C12P 19/34* (2006.01)
*C07H 21/00* (2006.01)
*C12N 15/10* (2006.01)

(52) U.S. Cl.
CPC .......... *C12N 15/1031* (2013.01); *C12P 19/34* (2013.01); *B01J 2219/005* (2013.01); *B01J 2219/00722* (2013.01)

(58) Field of Classification Search
CPC .............................. C07H 21/00; C12P 19/34
See application file for complete search history.

(56) References Cited

U.S. PATENT DOCUMENTS

| 5,541,061 A | 7/1996 | Fodor et al. |
| 5,639,603 A | 6/1997 | Dower et al. |
| 5,770,358 A | 6/1998 | Dower et al. |
| 5,942,609 A | 8/1999 | Hunkapiller et al. |
| 2007/0292954 A1 | 12/2007 | Elledge |

FOREIGN PATENT DOCUMENTS

| WO | WO-2010/025310 A2 | 3/2010 |
| WO | WO-2011056872 A2 | 5/2011 |
| WO | WO-2011066186 A1 | 6/2011 |
| WO | WO-2012/024351 A2 | 2/2012 |
| WO | 2012078312 | 6/2012 |
| WO | 2012103154 A1 | 8/2012 |
| WO | 2013032850 | 3/2013 |
| WO | WO-2014/151696 A1 | 9/2014 |

OTHER PUBLICATIONS

Stemmer et al., Gene 164 : 49 (1995).*
International Preliminary Report on Patentability issued in International Patent Application PCT/US2014/026261 dated Sep. 24, 2015.
Borovkov et al., "High-quality gene assembly directly from unpurified mixtures of microarray-synthesized oligonucleotides", Nucleic Acids Research, vol. 38, No. 19, Aug. 6, 2010.
Supplementary European Search Report in European Patent Application No. EP 14 76 9872 dated Oct. 12, 2016.
International Search Report for International Application No. PCT/2014/026261 dated Aug. 1, 2014.
Bar, G., Dendrimer-Modified Silicon Oxide Surfaces as Platforms for the Deposition of Gold and Silver Colloid Monolayers: Preparation Method, Characterization, and Correlation between Microstructure and Optical Properties, Langmuir, 12:1172-1179 (1996).
Bethell, D. et al., From monolayers to nanostructured materials: an organic chemists view of self-assembly, J. Electroanal. Chem., 409(1-2):137-143 (1996).
Colvin, V.L. et al., Semiconductor nanocrystals covalently bound to metal surfaces with self-assembled monolayers, J. Am. Chem. Soc., 114(13):5221-5230 (1992).
Grabar, K.C. et al., Preparation and Characterization of Au Colloid Monolayers, Analyt. Chem., 67(4):735-743 (1995).
Written Opinion for PCT/US2014/026261, 6 pages (dated Aug. 1, 2014).
Gibson, D.G., Enzymatic assembly of overlapping DNA fragments, Methods in Enzymology, 498: 349-361 (2011).

* cited by examiner

*Primary Examiner* — Ethan C Whisenant
(74) *Attorney, Agent, or Firm* — Choate, Hall & Stewart LLP; Brenda Hershbach Jarrell, JD; Robert N. Sahr, JD

(57) ABSTRACT

Aspects of the invention relate to methods, compositions for designing and producing a target nucleic acid. In particular, aspects of the invention relate to the multiplex synthesis of target polynucleotides.

14 Claims, 17 Drawing Sheets

Specification includes a Sequence Listing.

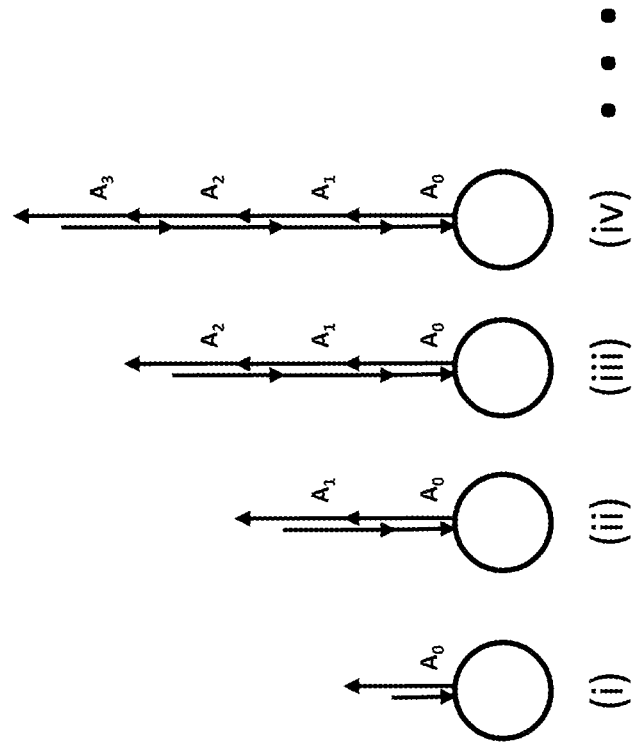
FIGURE 1C
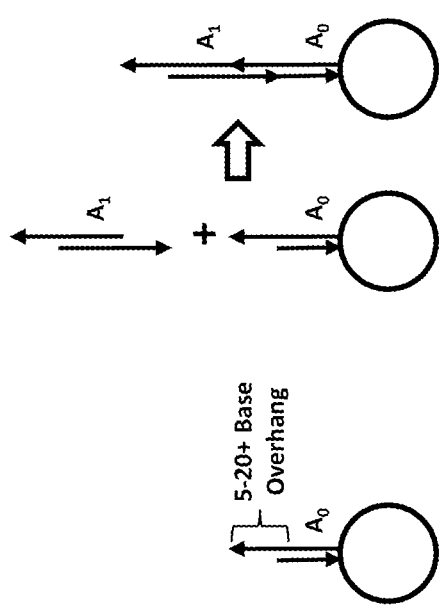
FIGURE 1B
FIGURE 1A

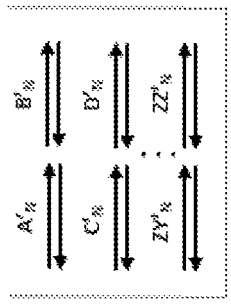
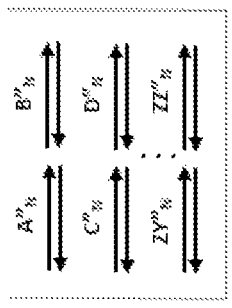
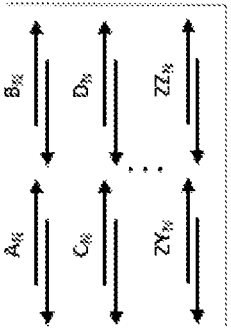
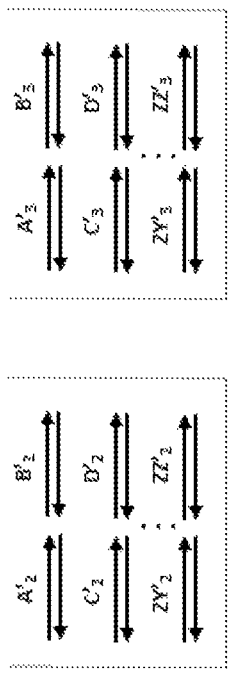
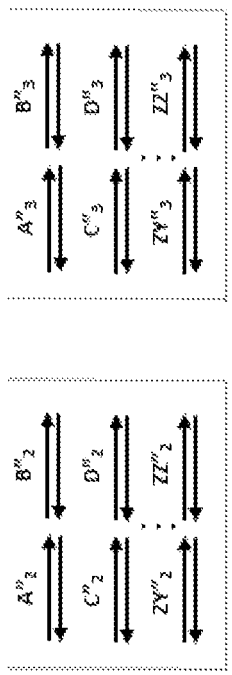
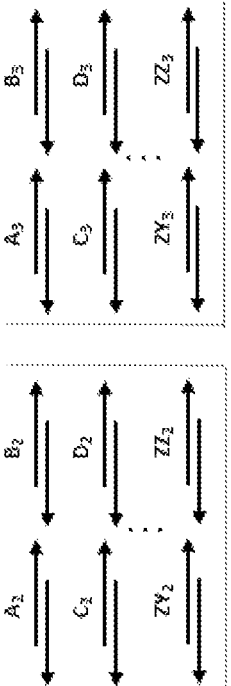
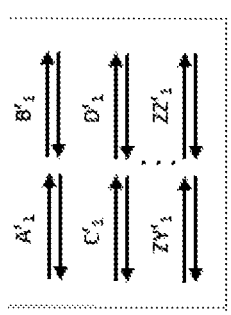
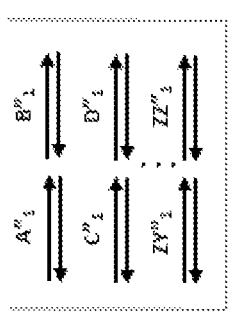
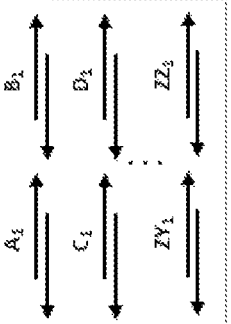
FIGURE 2A
FIGURE 2B
FIGURE 2C

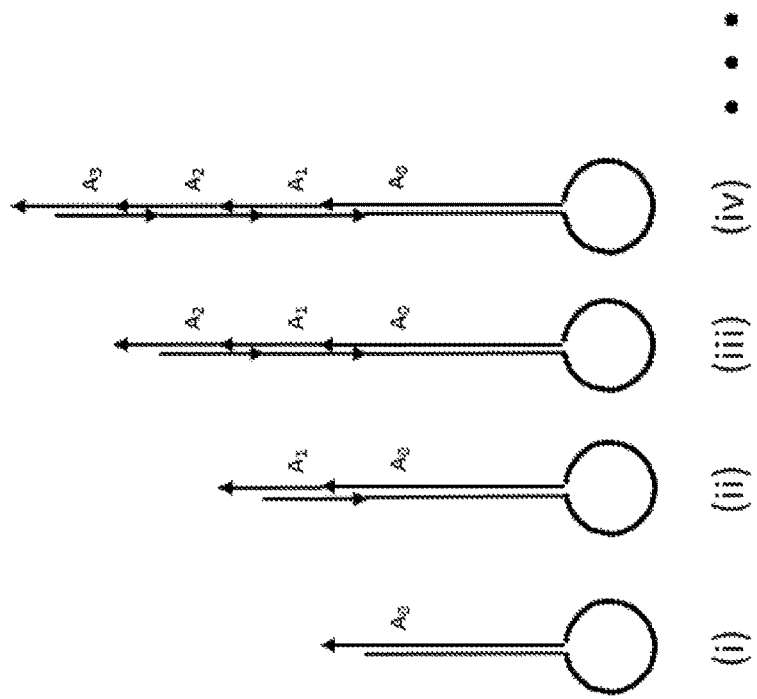
FIGURE 7C
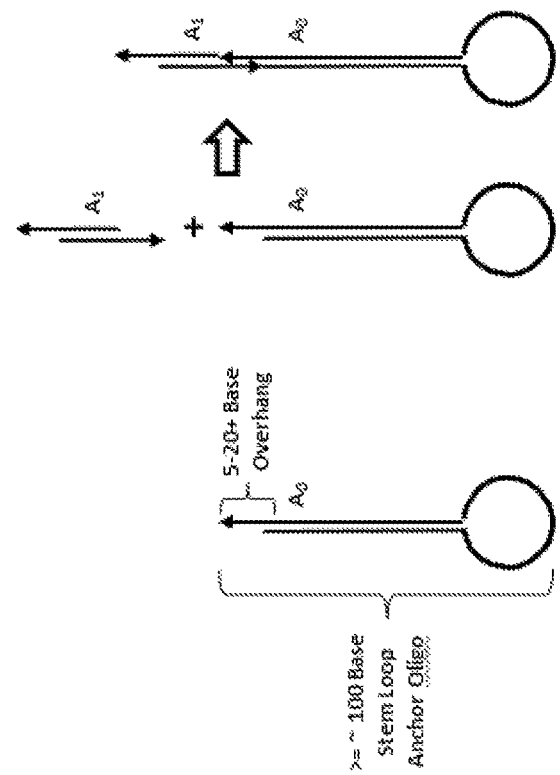
FIGURE 7B
FIGURE 7A

FIGURE 10B

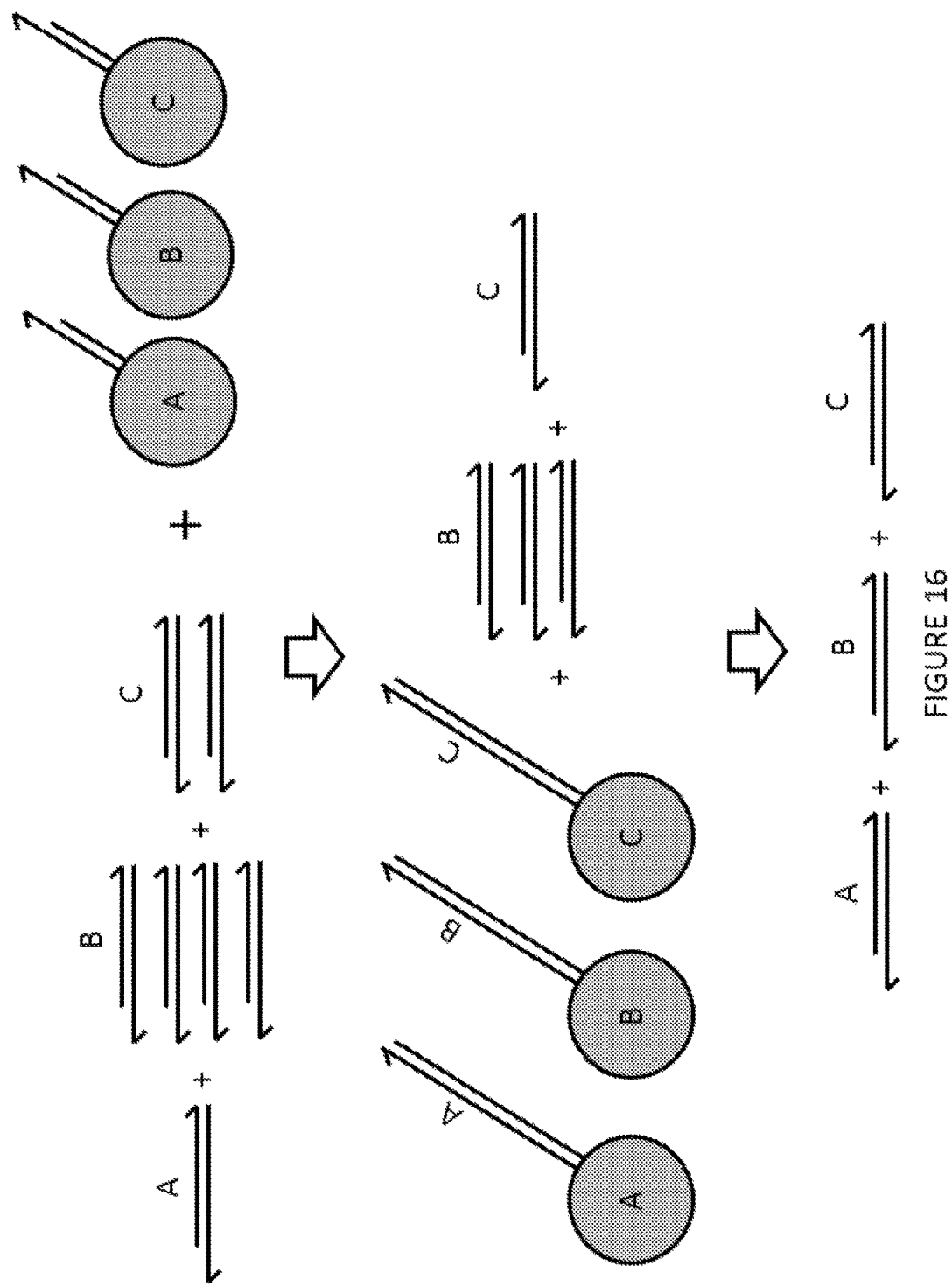

COMPOSITIONS AND METHODS FOR MULTIPLEX NUCLEIC ACIDS SYNTHESIS

RELATED APPLICATIONS

This application is a National Phase application of International Application No. PCT/US2014/026261, filed Mar. 13, 2014 which claims the benefit of and priority to U.S. Provisional Application No. 61/792,245, filed Mar. 15, 2013, the contents of each foregoing applications are incorporated herein by reference in their entirety.

REFERENCE TO SEQUENCE LISTING

This specification includes a sequence listing, submitted herewith, which includes the file entitled "127662-014001_ST25.txt" having the following size: 2.628 bytes which was created Mar. 13, 2014, the content of which is incorporated by reference herein.

FIELD OF THE INVENTION

Methods and compositions of the invention relate to nucleic acid assembly, and particularly to high fidelity, multiplex nucleic acid assembly reactions.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine. As such, high fidelity, low cost methods for synthesizing polynucleotides are needed.

In particular, currently there is significant interest in the chemical synthesis of polynucleotides for a wide range of applications including the synthesis of synthetic clones directly from genomic sequence data, the synthesis of large gene libraries and the synthesis of entire synthetic genomes. A major goal in the field of polynucleotide synthesis is the ability to synthesize large numbers of polynucleotides quickly and inexpensively. A significant part of the cost of polynucleotide synthesis is the cost of the reagents for carrying out the polynucleotide synthesis reactions. In order to lower this cost, reactions may be carried out in smaller volumes such as may be carried out in microfluidics.

SUMMARY OF THE INVENTION

Aspects of the invention relate to methods of producing at least one target nucleic acid. In some aspects of the invention, the methods provided allow for the synthesis of a plurality of different target molecules in a single reaction volume.

In one aspect, a method of producing at least one target nucleic acid having a predefined sequence is provided. The method includes: (a) providing a plurality of double-stranded anchor oligonucleotides having a first plurality of overhangs; (b) providing a plurality of double-stranded construction oligonucleotides having a second plurality of overhangs, wherein the second plurality of overhangs are designed to be complementary to the first plurality of overhangs; (c) hybridizing and ligating the anchor oligonucleotides with the construction oligonucleotides; and (d) optionally, repeating steps (a)-(c), thereby generating the at least one target nucleic acid. In some embodiments, the first plurality of overhangs is designed to be relatively mutually orthogonal to each other. The second plurality of overhangs can also be designed to be relatively mutually orthogonal to each other. In certain embodiments, the anchor oligonucleotides or at least a plurality of anchor oligonucleotides are attached to a support. The support can be solid, e.g., a bead. A stem loop polynucleotide can be used instead of a support. The anchor oligonucleotides can be immobilized to the same support, or each of the anchor oligonucleotides may be immobilized to a different support. In some embodiments, steps (a)-(d) are performed in a single reaction volume.

In another aspect, a method of producing at least one target nucleic acid having a predefined sequence can include: (a) ligating a first plurality of double-stranded oligonucleotides having a first plurality of overhangs with a second plurality of double-stranded oligonucleotides having a second plurality of overhangs, wherein the first plurality of overhangs are designed to be complementary to the second plurality of overhangs, thereby producing a first set of polynucleotides; (b) ligating a third plurality of double-stranded oligonucleotides having a third plurality of overhangs with a fourth plurality of double-stranded oligonucleotides having a fourth plurality of overhangs, wherein the third plurality of overhangs are designed to be complementary to the fourth plurality of overhangs, thereby producing a second set of polynucleotides; and (c) ligating the first set of polynucleotides with the second set of polynucleotides, wherein the first set of polynucleotides with the second set of polynucleotides are designed to have complementary overhangs, thereby forming at least one target nucleic acid. In some embodiments, the first, second, third and fourth pluralities of overhangs are each designed to be relatively mutually orthogonal to each other. The method may further comprise, optionally, repeating steps (a)-(c).

In a further aspect, a method of producing at least one target nucleic acid having a predefined sequence includes: ligating a first plurality of double-stranded oligonucleotides with a second plurality of double-stranded oligonucleotides at the 5' end of the second plurality of double-stranded oligonucleotides, and ligating the second plurality of double-stranded oligonucleotides with a third plurality of double-stranded oligonucleotides at the 3' end of the second plurality of double-stranded oligonucleotides, wherein the first plurality of double-stranded oligonucleotides have a first plurality of 3' overhangs, the second plurality of double-stranded oligonucleotides have a first plurality of 5' overhangs and a second plurality of 3' overhangs, and the third plurality of double-stranded oligonucleotides have a second plurality of 5' overhangs, wherein the first plurality of 3' overhangs are designed to be complementary to the first plurality of 5' overhangs, and the second plurality of 3' overhangs are designed to be complementary to the second plurality of 5' overhangs; thereby forming at least one target nucleic acid. In some embodiments, the first and second plurality of 5' and 3' overhangs are each designed to be relatively mutually orthogonal to each other. The method may further comprise, optionally, repeating the ligating step.

In yet another aspect, a method of producing a plurality of double-stranded oligonucleotides having a plurality of overhangs is provided. The method can include: (a) melting a first plurality of blunt-ended double-stranded oligonucleotides and a second plurality of blunt-ended double-stranded oligonucleotides to form a plurality of single-stranded oligonucleotides; and (b) re-annealing the plurality of single-stranded oligonucleotides to form a plurality of double-stranded oligonucleotides having a plurality of overhangs, wherein the plurality of overhangs are designed to be substantially mutually orthogonal to each other. In certain embodiments, the first and second pluralities of blunt-ended double-stranded oligonucleotides are error corrected or error reduced prior to melting.

In some aspects, the method comprises providing at least a plurality of support-bound double-stranded oligonucleotides comprising a single-stranded 5' overhang. The plurality of oligonucleotides can have a predefined sequence. In some embodiments, the single-stranded overhang comprises a sequence region at its 3' end that complementary to a sequence region of a 3' end of a first plurality of double-stranded construction oligonucleotides. In some embodiments, the method comprises providing at least a plurality of support-bound double-stranded oligonucleotides comprising a single-stranded 5' overhang, wherein the plurality of oligonucleotides has a predefined sequence, wherein the single-stranded overhang comprises a sequence region at its 3' end that is complementary to a sequence region of a 3' end of a first plurality of double-stranded construction oligonucleotides. In some embodiments, the method comprises generating at least a first plurality of double-stranded construction oligonucleotides comprising a single-stranded 3' overhang complementary to the plurality of support-bound oligonucleotides. In some embodiments, the method comprises hybridizing the at least first plurality of construction oligonucleotides to the plurality of support-bound oligonucleotides. In some embodiments, the method ligating the first plurality of construction oligonucleotides, and optionally repeating steps b-d thereby generating the at least target nucleic acid. In some embodiments, the step of ligating is in the presence of a ligase.

In some embodiments, in the step of providing, the at least plurality of support-bound double-stranded oligonucleotides comprises a plurality of different single-stranded 5' overhangs, each 5' overhangs being complementary to a plurality of different target nucleic acids. The overhang can be between 3 and 20 nucleotides long.

In some embodiments, the plurality of support-bound double-stranded oligonucleotides is immobilized to a single support, for example, a bead. In some embodiments, the plurality of target nucleic acids can be synthesized on a single support. Yet in other embodiments, each of the plurality of support-bound double-stranded oligonucleotides is immobilized to a different support thereby allowing the synthesis of a plurality of target nucleic acids, wherein each target nucleic acid is immobilized on a different support, for example, a bead. In various embodiments, the steps of synthesis are performed in a single reaction volume.

In some embodiments, the plurality of double-stranded construction oligonucleotides comprising a single-stranded overhang are generated by amplification of a support bound template oligonucleotides, each support bound template oligonucleotide having a 3' flanking sequence and a 5' flanking sequence, each flanking sequence having a primer binding site and a restriction enzyme recognition site. The flanking sequences can be cleaved off using a type IIS restriction enzyme. In some embodiments, the plurality of double-stranded construction oligonucleotides comprising a single-stranded overhang is generated by hybridizing partially complementary oligonucleotides. In some embodiments, the double-stranded construction oligonucleotides can be subjected to shuffling, and error reduction using for example, a mismatch binding protein.

In some embodiments, the plurality of double-stranded construction oligonucleotides comprises N pluralities of construction oligonucleotides, wherein the N pluralities of construction oligonucleotides span the entire sequence of the target nucleic acid without gaps.

According to some aspects of the invention, the method relates to the production of at least one target nucleic acid having a predefined sequence and comprises the step of providing N pluralities of double-stranded oligonucleotides comprising 3' overhangs, wherein the first plurality of oligonucleotides comprises at its 3' end a sequence region that is complementary to a sequence region at the 3' end of a second oligonucleotide, wherein a plurality of oligonucleotides N comprises at its 3' end a sequence region that is complementary to a sequence region of a plurality of oligonucleotides (N−1). The plurality of construction oligonucleotides can be hybridized and assembled pairwise through their unique overhangs. The assembled pairs of construction oligonucleotides can be ligated, using for example, a ligase. The steps can be repeated to hierarchically assemble the at least one target nucleic acid. In some embodiments, the synthesis of the target nucleic acids is performed in a single reaction volume.

According to some aspects of the invention, the method of producing at least one target nucleic acid having a predefined sequence comprises providing at least a plurality of stem-loop oligonucleotides comprising a 3' single-stranded overhang, wherein the single-stranded 3' overhang is complementary to a sequence region of a 3' end of a first plurality of double-stranded construction oligonucleotides. At least a first plurality of double-stranded construction oligonucleotides comprising a single-stranded 3' overhang complementary to the stem-loop oligonucleotides can be provided. The at least first plurality of construction oligonucleotides can be hybridized to the stem-loop oligonucleotides and ligated. Steps of synthesis can be repeated thereby generating the at least one target nucleic acid. In some embodiments, all steps are in a single reaction volume. In some embodiments, the overhang is between 3 and 20 nucleotides long. In some embodiments, the stem-loop oligonucleotide is at least 100 bps long.

In various embodiments, methods and compositions for synthesizing a plurality of polynucleotides within a single synthesis reaction volume are provided. Such methods are sometimes called multiplexed polynucleotide synthesis (MPS). Three categories of MPS are described in detail: I) Serial MPS, II) Hierarchical MPS and III) Parallel MPS.

BRIEF DESCRIPTION OF THE FIGURES

FIGS. 1A-1C illustrate a non-limiting exemplary method of serial multiplexed polynucleotide synthesis showing serial addition of oligonucleotide duplexes with overhangs. FIG. 1A illustrates a bead support comprising a support-bound or anchor oligonucleotide duplex having a unique 3' overhang. FIG. 1B illustrates the synthesis of a longer construct by the addition of an offset oligonucleotide duplex. FIG. 1C illustrates the synthesis of sub-assembly or full-length construct by consecutive additions of offset duplexes or dimers (i, ii, iii, iv).

FIGS. 2A-2C illustrate a non-limiting exemplary method of offset double-stranded oligonucleotides with overhangs preparation. FIG. 2A illustrates the generation of the the top strands (denoted by the symbol ['] prime) for each nucleic acid (e.g., gene) first, second, third, etc. of the offset dimers. FIG. 2B illustrates a similar set of reactions to generate the bottom strands of the offset dimers (denoted by symbol ["] double prime). FIG. 2C illustrates the pairwise combination of the top strands and bottom strands from the reaction wells corresponding to each gene's first, second, third, etc. offset dimers (top and bottom strand wells for the first offset dimer are mixed into a first offset dimer well, top and bottom strand wells for the second offset dimer are mixed into a second offset dimer well etc.).

FIGS. 7A-7C illustrate a non-limiting method of serial multiplexed polynucleotide synthesis using stem loop polynucleotide instead of a bead support. FIG. 7A illustrates a stem loop polynucleotide having a unique 3' overhang. FIG. 7B illustrates the synthesis of a longer construct by the addition of an offset oligonucleotide duplex to the stem loop polynucleotide. FIG. 7C illustrates the synthesis of sub-assembly or full-length construct by consecutive additions of offset duplexes or dimers (i, ii, iii, iv).

FIG. 10B illustrates a non-limiting exemplary sequence of offset dimers for multiplexed polynucleotide synthesis.

FIG. 13A is a schematic representation of 3 offset dimers A, B, and C, with an abundance of offset dimer B, which are designed to hybridize and ligate to a final product ABC. FIG. 13B is a schematic representation of 3 offset dimers A, B, and C If there is an abundance of offset dimer B and the termination reaction products AB and BC.

FIG. 16 illustrates a non-limiting exemplary method showing the use of bead based titration of overhanging oligonucleotide duplexes to reduce terminating reactions.

DETAILED DESCRIPTION OF THE INVENTION

Figure 3:
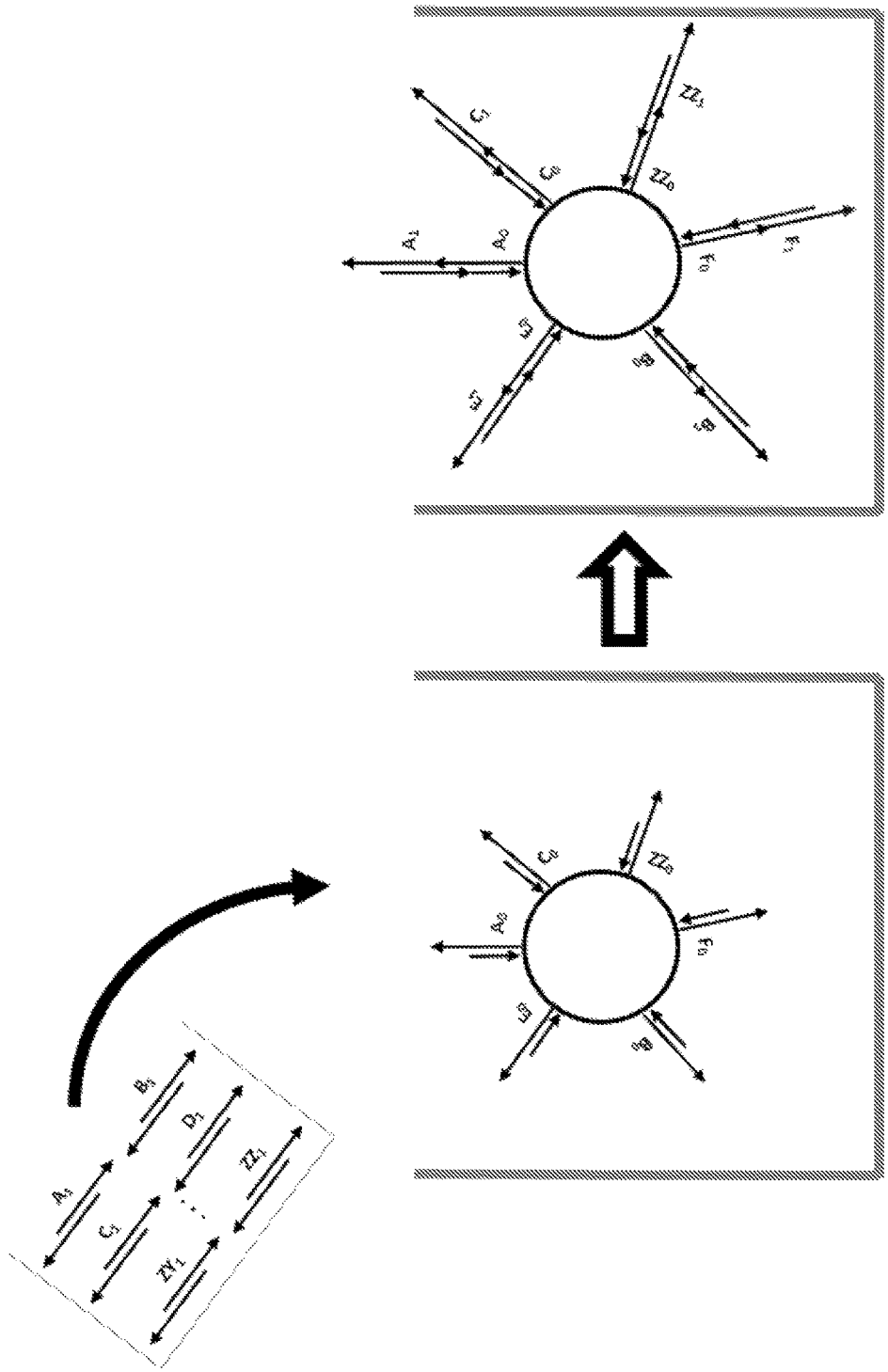
FIG. 3 illustrates a non-limiting exemplary method of serial multiplexed polynucleotide synthesis showing a first serial addition of overhanging oligonucleotide duplexes on a support (bead) with multiple anchor types per support.

Aspects of the invention can be used to assemble large numbers of nucleic acid fragments efficiently, and/or to reduce the number of steps required to generate large nucleic acid products, while reducing assembly error rate. Aspects of the invention can be incorporated into nucleic assembly procedures to increase assembly fidelity, throughput and/or efficiency, decrease cost, and/or reduce assembly time. In some embodiments, aspects of the invention may be automated and/or implemented in a high throughput assembly context to facilitate parallel production of many different target nucleic acid products.

Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example, forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to form an oligomer, a polymer or a compound composed of two or more members. The particular ordering of monomers within a polymer is referred to herein as the "sequence" of the polymer. The set of monomers includes, but is not limited to, for example, the set of common L-amino acids, the set of D-amino acids, the set of synthetic and/or natural amino acids, the set of nucleotides and the set of pentoses and hexoses. Aspects of the invention are described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predetermined sequence" or "predefined sequence" are used interchangeably and means that the sequence of the polymer is known and chosen before synthesis or assembly of the polymer. In particular, aspects of the invention are described herein primarily with regard to the preparation of nucleic acid molecules, the sequence of the nucleic acids being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotide constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein. In some embodiments, the assembly procedure may include several parallel and/or sequential reaction steps in which a plurality of different nucleic acids or oligonucleotides are synthesized or immobilized, primer-extended, and are combined in order to be assembled (e.g., by extension or ligation as described herein) to generate a longer nucleic acid product to be used for further assembly, cloning, or other applications.

In some embodiments, the methods and devices provided herein use oligonucleotides that are immobilized on a surface or substrate (e.g., support-bound oligonucleotides). Support-bound oligonucleotides comprise for example, oligonucleotides complementary to construction oligonucleotides, anchor oligonucleotides and/or spacer oligonucleotides. As used herein the terms "support", "substrate" and "surface" are used interchangeably and refer to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized in an array format. For example, single-stranded oligonucleotides are synthesized in situ on a common support, wherein each oligonucleotide is synthesized on a separate or discrete feature (or spot) on the substrate. In an embodiment, single-stranded oligonucleotides are bound to the surface of the support or feature. As used herein the term "array" refers to an arrangement of discrete features for storing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule on the array is localized to a known and defined location on the support. The sequence of each oligonucleotide can be determined from its position on the support. The array may comprise interfeatures regions. Interfeatures may not carry any oligonucleotide on their surface and may correspond to inert space.

In some embodiments, oligonucleotides are attached, spotted, immobilized, surface-bound, supported or synthesized on the discrete features of the surface or array. Some aspects of the invention relate to a polynucleotide assembly process wherein synthetic oligonucleotides are designed and used as templates for primer extension reactions, synthesis of complementary oligonucleotides and to assemble polynucleotides into longer polynucleotides constructs. In some embodiments, the method includes synthesizing a plurality of oligonucleotides or polynucleotides in a chain extension reaction using a first plurality of single-stranded oligonucleotides as templates. As noted above, the oligonucleotides may be first synthesized onto a plurality of discrete features of the surface, or on a plurality of supports (e.g., beads) or may be deposited on the plurality of features of the support or on the plurality of supports. The support may comprise at least 100, at least 1,000, at least $10^4$, at least $10^5$, at least $10^6$, at least $10^7$, at least $10^8$ features. In some embodiments, the oligonucleotides are covalently attached to the support. In some embodiments, the pluralities of oligonucleotides are immobilized to a solid surface.

In some embodiments, the support-bound oligonucleotides may be attached through their 5' end. Yet in other embodiments, the support-bound oligonucleotides are attached through their 3' end. In some embodiments, the support-bound oligonucleotides may be immobilized on the support via a nucleotide sequence (e.g., degenerate binding sequence), linker or spacer (e.g., photocleavable linker or chemical linker). It should be appreciated that by 3' end, it is meant the sequence downstream to the 5' end and by 5' end it is meant the sequence upstream to the 3' end. For example, an oligonucleotide may be immobilized on the support via a nucleotide sequence, linker or spacer that is not involved in hybridization. The 3' end sequence of the support-bound oligonucleotide referred then to a sequence upstream to the linker or spacer.

In certain embodiments, oligonucleotides may be designed to have a sequence that is identical or complementary to a different portion of the sequence of a predetermined target polynucleotide that is to be assembled. Accordingly, in some embodiments, each oligonucleotide may have a sequence that is identical or complementary to a portion of one of the two strands of a double-stranded target nucleic acid. As used herein, the term "complementary" refers to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The term "orthogonal" means that the sequences are different, non-interfering, or non-complementary.

In some embodiments, the plurality of construction oligonucleotides are designed such as each plurality of construction oligonucleotides comprise a sequence region at its 5' end that is complementary to sequence region of the 5' end of another construction oligonucleotide and a sequence region at its 3' end that is complementary to a sequence region at a 3' end of a different construction oligonucleotide. As used herein, a "construction" oligonucleotide refers to one of the plurality or population of single-stranded oligonucleotides used for polynucleotide assembly. The plurality of construction oligonucleotides comprises oligonucleotides for both the sense and antisense strand of the target polynucleotide. Construction oligonucleotides can have any length, the length being designed to accommodate an overlap or complementary sequence. Construction oligonucleotides can be of identical size or of different sizes. In preferred embodiments, the construction oligonucleotides span the entire sequence of the target polynucleotide without any gaps. Yet in other embodiments, the construction oligonucleotides are partially overlapping resulting in gaps between construction oligonucleotides when hybridized to each other. Preferably, the pool or population of construction oligonucleotides comprises construction oligonucleotides having overlapping sequences so that construction oligonucleotides can hybridize to one another under the appropriate hybridization conditions. One would appreciate that each internal construction oligonucleotides will hybridize to two different construction oligonucleotide whereas the construction oligonucleotides at the 5' and/or 3' end will hybridize each to a different (or the same) internal oligonucleotide(s). Hybridization and ligation of the overlapping construction oligonucleotides will therefore result in a target polynucleotide having a 3' and/or a 5' overhang. Yet in some embodiments, the resulting target polynucleotide may comprise blunt end at its 5' or/and 3' terminus. In some embodiments, if the target polynucleotide is assembled from N construction oligonucleotides, 1 to N pluralities of different support-bound single-stranded oligonucleotides are designed such as the first plurality of construction oligonucleotides comprises at its 3' end a sequence region that is complementary to a sequence region at the 3' end of an anchor oligonucleotide and wherein a N plurality of construction oligonucleotides comprises at its 3' end a sequence region that is complementary to a 3' end sequence region of the (N−1) construction oligonucleotide. In some embodiments, the first plurality of oligonucleotides has a 5' end that is complementary to the 5' end of a support bound anchor single-stranded oligonucleotide.

As used herein, the term "anchor oligonucleotide" refers to an oligonucleotide designed to be complementary to at least a portion of the target polynucleotide and may be immobilized on the support. In an exemplary embodiment, the anchor may be immobilized on the support through its 5' end.

As used herein, the term "dimer" refers to an oligonucleotide duplex or double-stranded oligonucleotide molecule. The term "offset dimer" refers to an oligonucleotide duplex having a 3' or 5' overhang (i.e., non-blunt end). In some embodiments, anchor and/or construction oligonucleotides can be double-stranded and have a 3' and/or a 5' overhang.

It should be appreciated that different oligonucleotides may be designed to have different lengths with overlapping sequence regions. Overlapping sequence regions may be identical (i.e., corresponding to the same strand of the nucleic acid fragment) or complementary (i.e., corresponding to complementary strands of the nucleic acid fragment). Overlapping sequences may be of any suitable length. Overlapping sequences may be between about 5 and about 500 nucleotides long (e.g., between about 10 and 100, between about 10 and 75, between about 10 and 50, about 20, about 25, about 30, about 35, about 40, about 45, about 50, about 100, about 200, about 300, about 400, about 500 etc. . . . nucleotides long). However, shorter, longer or intermediate overlapping lengths may be used. It should be appreciated that overlaps (5' or 3' regions) between different input nucleic acids used in an assembly reaction may have different lengths. In some embodiments, anchor support-bound (or immobilized) oligonucleotides include sequence regions having overlapping regions to assist in the assembly of a predetermined nucleic acid sequence. In a preferred embodiment, anchor oligonucleotides include sequence regions having complementary regions for hybridization to a different oligonucleotide or to a polynucleotide (such as, for example, a sub-assembly product). The complementary regions refer to a sequence region at either a 3' end or a 5' end of the immobilized template oligonucleotide (e.g., template oligonucleotide). In some embodiments, the complementary region is localized at the 3' end of the anchor oligonucleotides. Complementary regions refer to a 3' end or a 5' end region of a first oligonucleotide or polynucleotide that is capable of hybridizing to a 5' end or 3' end of a second oligonucleotide or polynucleotide.

In some embodiments, nucleic acids are assembled using ligase-based assembly techniques, wherein the oligonucleotides are designed to provide full length sense (or plus strand) and antisense (or minus strand) strands of the target polynucleotide construct. After hybridization of the sense and antisense oligonucleotides, the oligonucleotides on each strand are subjected to ligation in order to form the target polynucleotide construct or a sub-assembly product. Reference is made to U.S. Pat. No. 5,942,609, which is incorporated herein in its entirety. Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid. A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), Ampliligase® (available from Epicenter Biotechnologies) any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures. Non-enzymatic techniques, for example chemical ligation, can be used to ligate nucleic acids.

Multiplex Polynucleotide Synthesis

There is presently a significant interest in the chemical synthesis of polynucleotides for a wide range of applications. Such applications include the synthesis of synthetic clones directly from genomic sequence data, the synthesis of large gene libraries and the synthesis of entire synthetic genomes. One of the major goal in the field of polynucleotide synthesis is the ability to synthesize large numbers of polynucleotides quickly and inexpensively. It should be appreciated that a significant part of the cost of polynucleotide synthesis is the cost of the reagents for carrying out the polynucleotide synthesis reactions. In order to lower this cost, reactions may be carried out in smaller volumes. For example, reactions may be carried in microfluidics. Alternatively, and as described in some aspects of the invention, a plurality of different polynucleotides can be synthesized within a single synthesis reaction volume in a multiplexed polynucleotide synthesis.

Certain embodiments of multiplex nucleic acid assembly reactions for generating a plurality of nucleic acids having a predetermined sequence are illustrated with reference to FIGS. 1-16. It should be appreciated that synthesis and assembly methods described herein (including, for example, oligonucleotide synthesis, step-wise assembly, multiplex nucleic acid assembly, hierarchical assembly of nucleic acid fragments, or any combination thereof) may be performed in any suitable format, including in a reaction tube, in a multi-well plate, on a surface, on a column, in a microfluidic device (e.g., a microfluidic tube), a capillary tube, etc.

A predetermined nucleic acid fragment may be assembled from a plurality of different starting nucleic acids (e.g., oligonucleotides) in a multiplex assembly reaction (e.g., a multiplex enzyme-mediated reaction, a multiplex chemical assembly reaction, or a combination thereof). Certain aspects of multiplex nucleic acid assembly reactions are illustrated by the following description of certain embodiments of multiplex oligonucleotide assembly reactions. It should be appreciated that the description of the assembly reactions in the context of oligonucleotides is not intended to be limiting. The assembly reactions described herein may be performed using starting nucleic acids obtained from one or more different sources (e.g., synthetic or natural polynucleotides, nucleic acid amplification products, nucleic acid degradation products, oligonucleotides, etc.). The starting nucleic acids may be referred to as assembly nucleic acids (e.g., assembly oligonucleotides). As used herein, an assembly nucleic acid has a sequence that is designed to be incorporated into the nucleic acid product generated during the assembly process. However, it should be appreciated that the description of the assembly reactions in the context of double-stranded nucleic acids is not intended to be limiting. In some embodiments, one or more of the starting nucleic acids illustrated in the figures and described herein may be provided as single-stranded nucleic acids. Accordingly, it should be appreciated that where the figures and description illustrate the assembly of cohesive-end double-stranded nucleic acids, the presence of one or more single-stranded nucleic acids is contemplated.

According to various embodiments, the target nucleic acid can be divided first into two or more overlapping nucleic acid fragments (or subassembly fragments). Each nucleic acid fragments is then subdivided into two or more overlapping smaller nucleic acid fragments. In some embodiments, the target nucleic acid can be assembled by recursive assembly or hierarchical assembly, serial assembly or parallel assembly.

Oligonucleotides may be synthesized using any suitable technique. For example, oligonucleotides may be synthesized on a column or other support (e.g., a chip). Examples of chip-based synthesis techniques include techniques used in synthesis devices or methods available from CombiMatrix, Agilent, Affymetrix, or other sources. A synthetic oligonucleotide may be of any suitable size, for example between 10 and 1,000 nucleotides long (e.g., between 10 and 200, 200 and 500, 500 and 1,000 nucleotides long, or any combination thereof). An assembly reaction may include a plurality of oligonucleotides, each of which independently may be between 10 and 300 nucleotides in length (e.g., between 20 and 250, between 30 and 200, 50 to 150, 50 to 100, or any intermediate number of nucleotides). However, one or more shorter or longer oligonucleotides may be used in certain embodiments.

As used herein, an oligonucleotide may be a nucleic acid molecule comprising at least two covalently bonded nucleotide residues. In some embodiments, an oligonucleotide may be between 10 and 1,000 nucleotides long. For example, an oligonucleotide may be between 10 and 500 nucleotides long, or between 500 and 1,000 nucleotides long. In some embodiments, an oligonucleotide may be between about 20 and about 300 nucleotides long (e.g., from about 30 to 250, 40 to 220, 50 to 200, 60 to 180, or about 65 or about 150 nucleotides long), between about 100 and about 200, between about 200 and about 300 nucleotides, between about 300 and about 400, or between about 400 and about 500 nucleotides long. However, shorter or longer oligonucleotides may be used. An oligonucleotide may be a single-stranded nucleic acid. However, in some embodiments a double-stranded oligonucleotide may be used as described herein. In certain embodiments, an oligonucleotide may be chemically synthesized as described in more detail below. In some embodiments, an input nucleic acid (e.g., synthetic oligonucleotide) may be amplified before use. The resulting product may be double-stranded.

In certain embodiments, each oligonucleotide may be designed to have a sequence that is identical to a different portion of the sequence of a predetermined target nucleic acid that is to be assembled. Accordingly, in some embodiments each oligonucleotide may have a sequence that is identical to a portion of one of the two strands of a double-stranded target nucleic acid. For clarity, the two complementary strands of a double stranded nucleic acid are referred to herein as the positive (P) and negative (N) strands. This designation is not intended to imply that the strands are sense and anti-sense strands of a coding sequence. They refer only to the two complementary strands of a nucleic acid (e.g., a target nucleic acid, an intermediate nucleic acid fragment, etc.) regardless of the sequence or function of the nucleic acid. Accordingly, in some embodiments a P strand may be a sense strand of a coding sequence, whereas in other embodiments a P strand may be an anti-sense strand of a coding sequence. It should be appreciated that the reference to complementary nucleic acids or complementary nucleic acid regions herein refers to nucleic acids or regions thereof that have sequences which are reverse complements of each other so that they can hybridize in an antiparallel fashion typical of natural DNA.

According to one aspect of the invention, a target nucleic acid may be either the P strand, the N strand, or a double-stranded nucleic acid comprising both the P and N strands. It should be appreciated that different oligonucleotides may be designed to have different lengths. In some embodiments, one or more different oligonucleotides may have overlapping sequence regions (e.g., overlapping 5' regions and/or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 2 and about 50 (e.g., between 3 and 20, between 3 and 10, between 3 and 8, or 4, 5, 6, 7, 8, 9, etc. nucleotides long). However, shorter, longer or intermediate overlapping lengths may be used. It should be appreciated that overlaps between different input nucleic acids used in an assembly reaction may have different lengths and/or sequences. For example, the overlapping sequences may be different than one another by at least one nucleotide, 2 nucleotides, 3 nucleotides, or more. Assuming that the overlapping sequences differ from one another by x nucleotides, then up to (4x+1) pieces of different input nucleic acids can be assembled together in one reaction.

In a multiplex oligonucleotide assembly reaction designed to generate a predetermined nucleic acid fragment, the combined sequences of the different oligonucleotides in the reaction may span the sequence of the entire nucleic acid fragment on either the positive strand, the negative strand, both strands, or a combination of portions of the positive strand and portions of the negative strand. The plurality of different oligonucleotides may provide either positive sequences, negative sequences, or a combination of both positive and negative sequences corresponding to the entire sequence of the nucleic acid fragment to be assembled. In some embodiments, the plurality of oligonucleotides may include one or more oligonucleotides having sequences identical to one or more portions of the positive sequence, and one or more oligonucleotides having sequences that are identical to one or more portions of the negative sequence of the nucleic acid fragment. One or more pairs of different oligonucleotides may include sequences that are identical to overlapping portions of the predetermined nucleic acid fragment sequence as described herein (e.g., overlapping sequence portions from the same or from complementary strands of the nucleic acid fragment). In some embodiments, the plurality of oligonucleotides includes a set of oligonucleotides having sequences that combine to span the entire positive sequence and a set of oligonucleotides having sequences that combine to span the entire negative sequence of the predetermined nucleic acid fragment. However, in certain embodiments, the plurality of oligonucleotides may include one or more oligonucleotides with sequences that are identical to sequence portions on one strand (either the positive or negative strand) of the nucleic acid fragment, but no oligonucleotides with sequences that are complementary to those sequence portions. In one embodiment, a plurality of oligonucleotides includes only oligonucleotides having sequences identical to portions of the positive sequence of the predetermined nucleic acid fragment. In one embodiment, a plurality of oligonucleotides includes only oligonucleotides having sequences identical to portions of the negative sequence of the predetermined nucleic acid fragment. These oligonucleotides may be assembled by sequential ligation or in an extension-based reaction (e.g., if an oligonucleotide having a 3' region that is complementary to one of the plurality of oligonucleotides is added to the reaction).

In one aspect, a nucleic acid fragment may be assembled in a ligase-mediated assembly reaction from a plurality of oligonucleotides that are combined and ligated in one or more rounds of ligase-mediated ligations. Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid).

One should appreciate that the multiplex polynucleotide assembly reactions can take place in a single volume, for example in a well, or can take place in a localized individual microvolume. In some embodiments, the extension and/or assembly reactions are performed within a microdroplet (see PCT Application PCT/US2009/55267 and PCT Application PCT/US2010/055298, each of which is incorporate herein by reference in their entirety).

Generation of Multiplexed Offset Duplex

Some aspects of the invention relate to offset duplex (also referred herein as offset dimers) of dimer generation for assembly using cohesive ends. FIG. 2 shows an exemplary method for Multiplexed Offset Duplex (or Dimers) Preparation. FIG. 2 details the multiplexed preparation of the offset dimer building blocks (double-stranded overhanging oligonucleotides). For example, as illustrated in FIG. 2, 3N reactions can be take place. In an exemplary embodiment, for a 2 kb mer, N=20 and 60 reaction wells can be used. Referring to FIG. 2A, the top strands (denoted by the symbol ['] prime) for each nucleic acid (e.g., gene) first, second, third, etc. of the offset dimers can be generated by amplification of support-bound template oligonucleotides (e.g., from chip) such that there is a single reaction for each gene's first offset dimer, a second reaction for each genes second offset dimer etc. The number of top strand reactions can scale as N, where N is the number of pieces making up the final nucleic acid construct (e.g., for a 2 Kb mer with 100 bp pieces, N would be 20). In some embodiments, the template support-bound oligonucleotides can be designed to have 5' and 3' amplification sequences, for example universal amplification tags. Error correction may be carried out and universal amplification tags may be removed. Referring to FIG. 2B, a similar set of reactions can be carried out for the bottom strands of the offset dimers (denoted by symbol ["] double prime). At this point error correction may be carried out and universal amplification tags may be removed. For example, amplification tags can be removed using a Type IIS restriction enzyme. Referring to FIG. 2C, the top strands and bottom strands from the reaction wells corresponding to each gene's first, second, third, etc. offset dimers are mixed in pairwise fashion (top and bottom strand wells for the first offset dimer are mixed into a first offset dimer well, top and bottom strand wells for the second offset dimer are mixed into a second offset dimer well etc.). The resulting product can then be melted and re-annealed to form corresponding offset dimers.

One should appreciate that the variation in the concentration of individual fragments to be assembled might result into the assembly of incomplete intermediate constructs. For example, in the assembly of the target nucleic acid sequence (ABCDEF) using oligonucleotides A, B, C, D, E, F, each of which having the appropriate cohesive overhang end, if the concentration of the individual fragments is not equimolar (e.g., if the concentration of A, B and C is greater than the concentration of D, E and F), terminating species (such as AB and BC) can be formed resulting in a mixture of unligated intermediate products. To avoid the formation of incomplete intermediate constructs, the target nucleic acid can be assembled from at least two pools of individual fragments (e.g., pool 1: A, C, E and Pool 2: B, D, F). In some embodiments, each of the two pools comprises a plurality of nucleic acid fragments, each nucleic acid fragment of the first pool having a terminal end complementary to a terminal end of a nucleic acid fragment in the second pool. In some embodiments, the at least two pools can be formed by splitting the population of oligonucleotides into the at least two pools and amplifying the oligonucleotides in each pool separately. In other embodiments, the at least two pools can be formed by releasing (e.g., by eluting, cleaving or amplifying) oligonucleotides from a first oligonucleotide array into a first pool and releasing the oligonucleotides of a second oligonucleotide array into a second pool. Yet in another embodiment, the at least two different pools can be formed by amplifying oligonucleotide sequences using at least two different sets of amplification tags as described herein. By the way of example, the second pool comprising oligonucleotides B, D and F can be diluted such as the molar concentration of the oligonucleotides B, D, and F present in the second pool is lower than the molar concentration of oligonucleotides A, C, and E present in the first pool. For example, the molar concentration of the oligonucleotides in the second pool may be about two times, 10 times, 20 times, 50 times, 100 times or more lower than the molar concentration of the oligonucleotides in the first pool. After mixing and ligating the two pools, the resulting product comprises the target nucleic acid having the predetermined sequence and can be separated from the excess oligonucleotides form the first pool. In certain embodiments, it may be desirable to form pools of oligonucleotide dimers having different molar concentrations. For example, the assembly of the target nucleic acid sequences ABCDEFGH can be carried out using at least two different pools, the first pool comprising oligonucleotides A, B, E, F and the second pool comprising oligonucleotides C, D, G, H. The second pool can be diluted such that the molar concentration of oligonucleotides C, D, G, H is lower (e.g 10 times or 100 times) than the molar concentration of oligonucleotides A, B, E, F. Oligonucleotides having the appropriate cohesive overhang ends can be ligated to form the intermediate products AB and EF in the first pool and CD and GH in the second pool. Since the molar concentration of C, D, G, H is lower than the molar concentration of A, B, E. F, the molar concentration of CD and GH is lower than the molar concentration of AB and EF. After mixing the intermediates products AB, CD, EF, GH under ligating conditions, the resulting product comprising the target nucleic acid having the predetermined sequence can be separated from the excess dimers AB and EF.

Serial Multiplexed Polynucleotide Synthesis (Serial MPS)

In some embodiments, beads are employed which have on them a plurality of double-stranded anchor oligonucleotides with attachment overhangs corresponding to N different desired polynucleotides (e.g., polynucleotides A, B, C, D . . . N) to which subsequent sets of construct oligonucleotides, designed to hybridize and ligate to said anchor oligonucleotides, are sequentially added. The construct oligonucleotides can include double-stranded oligonucleotides with overhangs and can be prepared in separate pools. For example, a first pool can contain all first construct oligonucleotides {A1, B1, C1, D1 . . . N1}, and a second pool can contain all second construct oligonucleotides {A2, B2, C2, D2, . . . N2} etc. . . . corresponding to the desired N different polynucleotides. The oligonucleotides can be designed such that A1 hybridizes to polynucleotide A's anchor oligonucleotide forming a gapless ligatable junction and is orthogonal to all other oligonucleotide anchors. Likewise A2 is designed to hybridize to A1 forming a gapless ligatable junction and is orthogonal to all other oligonucleotides in solution.

In order to synthesize a plurality of polynucleotides in a single reaction volume, a set of serial additions and washes can be carried out. In some embodiments, all first double-stranded, overhanging first construct oligonucleotides {A1, B1, C1, D1, . . . N1} are added to anchors {A0, B0, C0, D0, . . . N0}, hybridized and washed to form {A0A1, B0B1, C0C1, D0D1, . . . N0N1}. Next second double stranded overhanging construct oligonucleotides {A2, B2, C2, D2 . . . N2} are added, hybridized, ligated and washed to form {A0A1A2, B0B1B2, C0C1C2, D0D1D2, . . . N0N1N2}. This process can be repeated until the desired length set of N polynucleotides is formed.

As an example N may be 100 polynucleotides, each polynucleotide having a length of 1000 nucleotide base pairs (1 Kbp). In an exemplary embodiment, each overhanging polynucleotide may be 100 bp in length. In such embodiment, approximately 10 serial additions of oligonucleotides {A1, B1, C1, D1 . . . N1} through {A10, B10, C10, D10, . . . N10} would be required in order to construct the desired N polynucleotides of length 1 Kbp. In this example, the total number of hybridization junctions is 100 different polynucleotides*10 oligonucleotides per polynucleotide=1000. The total number of nucleotide base pairs synthesized per reaction volume would be: 100 polynucleotides*1000 bp=100,000 bp. In a typical gene synthesis, assembly reaction a 10 µL microplate reaction volume can be used to assemble a single 1000 bp gene. In this example of multiplexed polynucleotide assembly, the same reaction volume (10 µL) can be used to assemble 100*1000 bp which gives an effective reaction volume of 100 nL per 1000 bp gene. In some embodiments, the methods to create the overhangs result in molecules having different types of overhangs. For example, some moelcules can have the first strand as an overhang, while others can have the other reverse complement strand as the overhang. In order that the double-stranded overhangs of the constituent oligonucleotides not to cross hybridize they require having a coding space equal at least to twice the total number of hybridization junctions (e.g., 2,000). In certain embodiments, the coding space for the overhangs should be greater than the total number of nucleotides base pairs synthesize per reaction volume (e.g., 100,000). These two examples correspond to a minimum double-stranded overhang length of not less than: Log 4 (2*N*M) (e.g., a 6 base overhang for N=100 and M=10, where M is the number of oligonucleotides per polynucleotide; or preferably, Log 4 (N*L) where L is the length of the polynucleotide (e.g., a 9 base overhang for N=100 and L=1000 bp), as in general L is much larger than M.

In another exemplary embodiment, N=1000 and L=1000 bp comprising 1000 polynucleotides per well and 1 Million synthesized bps per well. State-of-the-art microtitre plate processing can take place in ~1 µL volumes. In this example of multiplexed polynucleotide assembly, 1000*1000 bps can be assembled in such a single reaction volume, which would correspond to a ~1 nL reaction volume per 1000 bps construct.

In order to harvest individual polynucleotides, primer pairs corresponding to polynucleotides of interest may be prepared and used to amplify out polynucleotides of interest. Alternatively separate flanking amplification tags corresponding to the N individual polynucleotides may be incorporated into each of the N individual polynucleotide and primer pairs from a reusable library may be used to amplify out desired polynucleotides.

In an alternate variation of serial MPS, the anchor oligonucleotides on the beads can all have an identical overhang attachment sequence comprising a universal anchor. In this example, each of the first set of construct oligonucleotides ({A1, B1, C1, D1, . . . N1}) can have one end designed to attach to the universal anchor. After ligation of the first set of construct oligonucleotides, construct oligonucleotides can be subsequently added. The design of those oligonucleotides can be identical to the serial MPS process discussed above.

FIG. 1 shows an exemplary method for producing polynucleotide having a predetermined sequence on a substrate or solid support (e.g., bead) by serial addition of oligonucleotide duplexes with overhangs. Referring to FIG. 1A, a bead support is shown; each bead comprising a support-bound or anchor oligonucleotide duplex having a unique 3' overhang. In some embodiments, each bead carried a different anchor oligonucleotide corresponding to N different desired polynucleotides (e.g., polynucleotides A, B, C, D . . . N) to be synthesized. In some embodiments, the overhang is from about 5 to 20 or more bases long. In some embodiments, the immobilized duplex can be generated by hybridization of an oligonucleotide having a 3' sequence complementary to the 5' end sequence of an immobilized anchor oligonucleotide so as to generate an anchor duplex having a unique free 3' overhang (also referred herein as stub). In some embodiments, the anchor oligonucleotide can be immobilized on the bead support through its 5' end. Referring to FIG. 1B, in a next step, an additional offset (i.e., overhanging) oligonucleotide duplex is added to allow the synthesis of a longer construct. Referring to FIG. 1C, consecutive additions of offset duplexes or dimers (i, ii, iii, iv) allow for the synthesis of a sub-assembly or full-length construct. In some embodiments, the plurality of immobilized duplexes can be ligated. For example, ligation can be performed using a ligase at each addition step. A wash step can be introduced in between each addition step. Alternatively, a ligase may be added concurrently. In some embodiments, offset duplexes can be introduced in abundance to the number of anchor stub binding groups on each bead. In some embodiments, the final constructs may be harvested from each bead using gene specific amplification from the bead surface. For example, primers that are specific of the target polynucleotide to be synthesized can be added so as to amplify the target polynucleotide.

Figure 4:
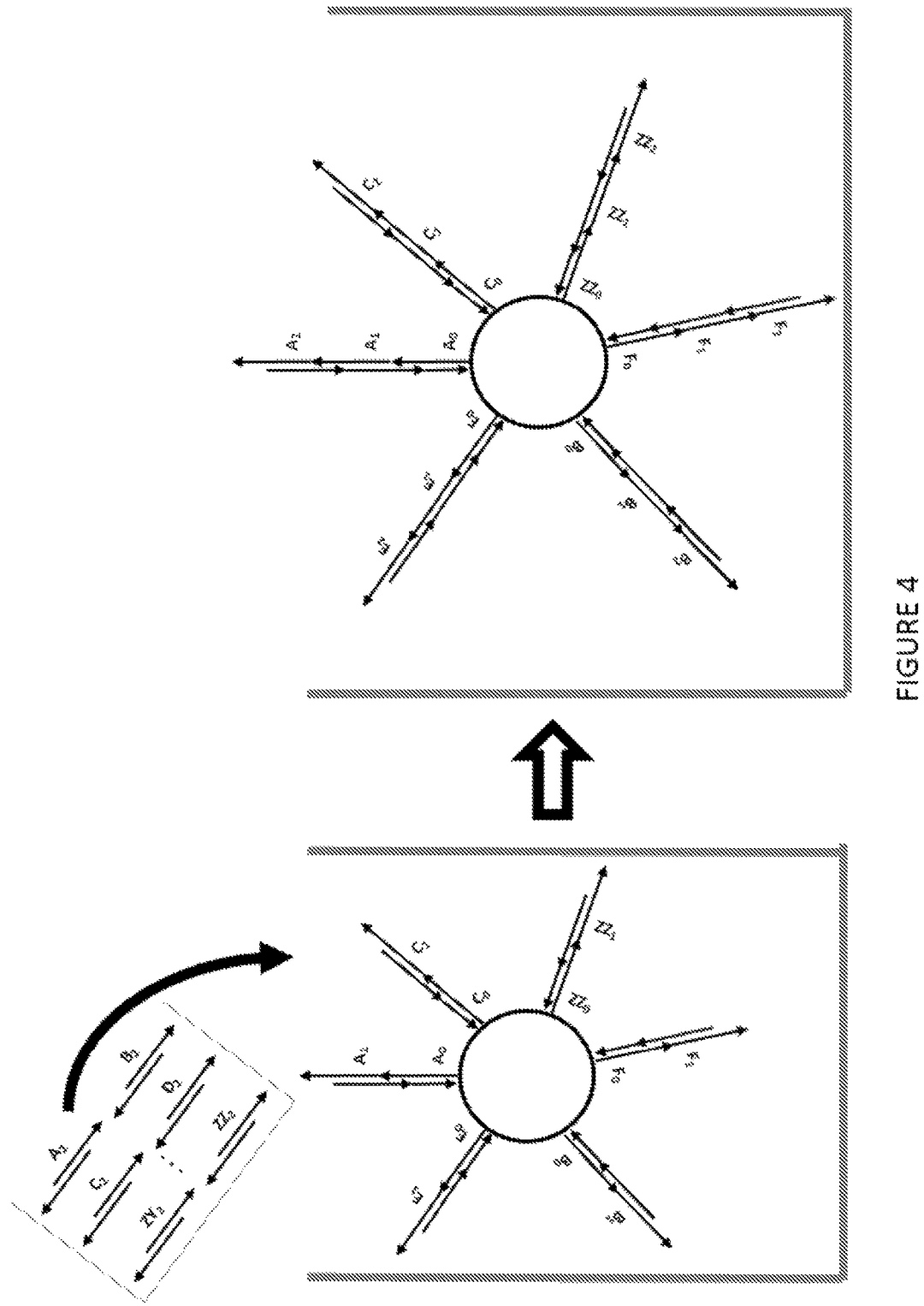
FIG. 4 illustrates a non-limiting exemplary method of serial multiplexed polynucleotide synthesis showing a second serial addition of overhanging oligonucleotide duplexes on a support (bead) with multiple anchor types per support.
Figure 5:
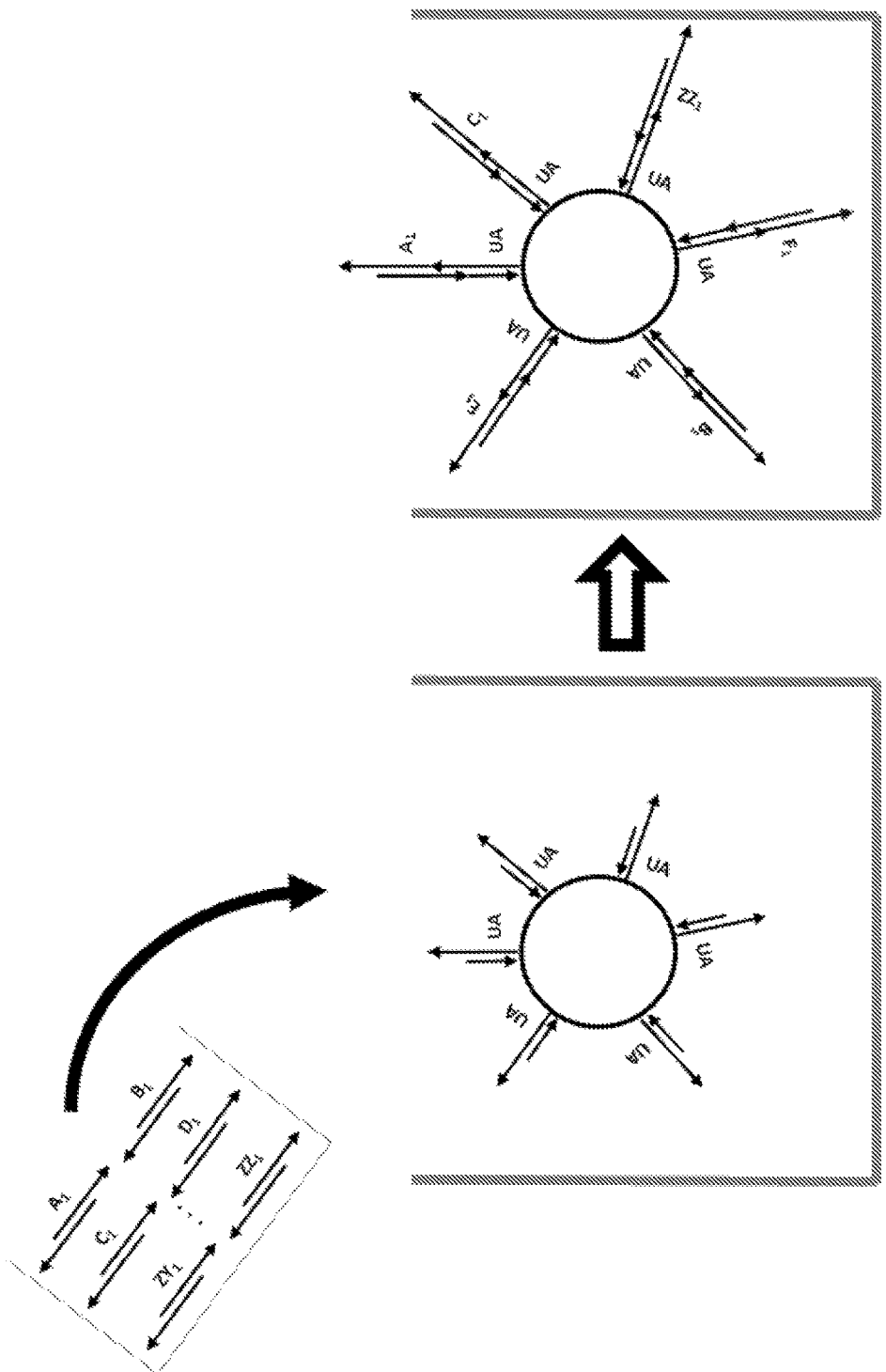
FIG. 5 illustrates a non-limiting exemplary method of serial multiplexed polynucleotide synthesis showing a first serial addition of overhanging oligonucleotide duplexes on a support (bead) with a universal anchor.
Figure 6:
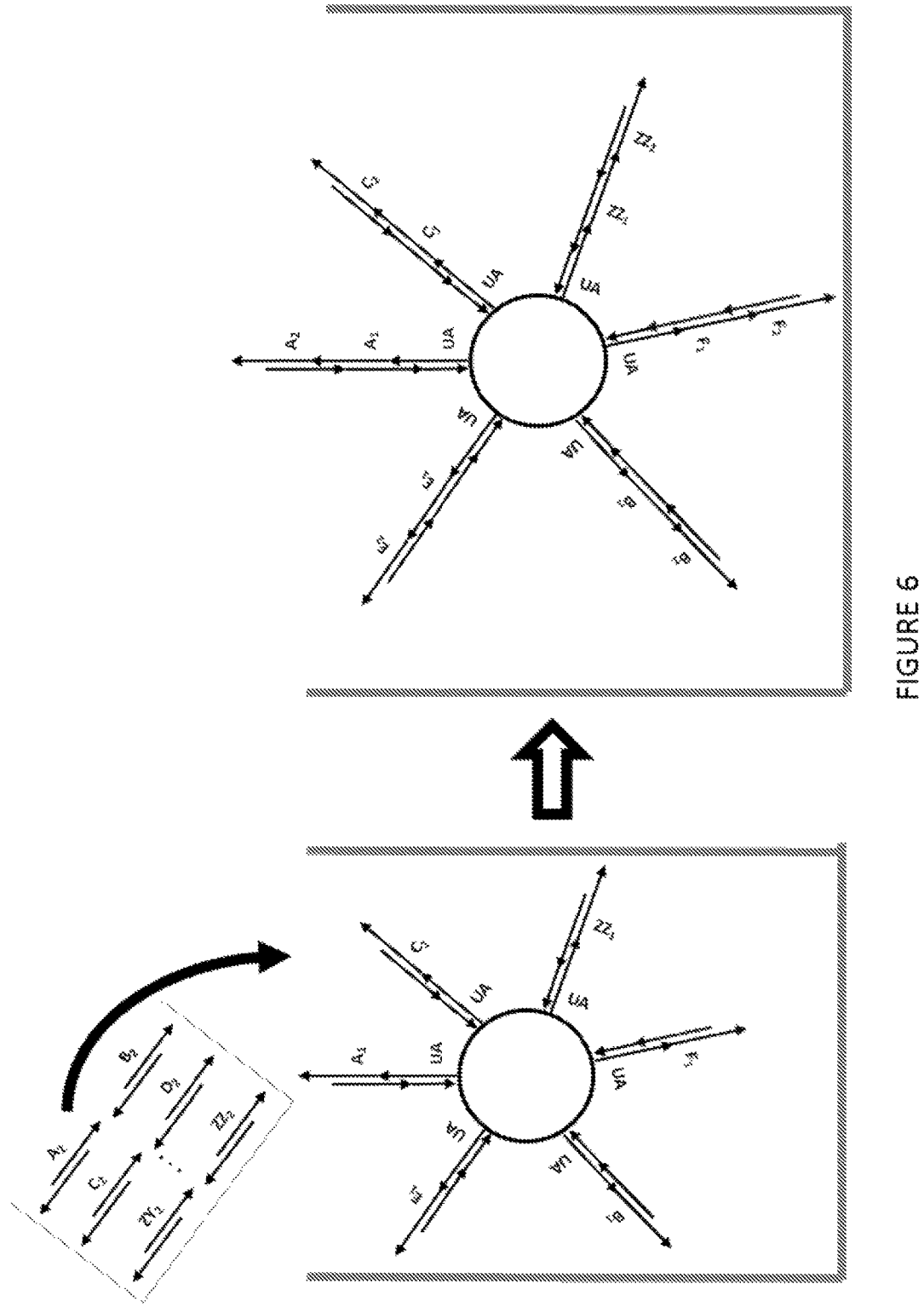
FIG. 6 illustrates a non-limiting exemplary method of serial multiplexed polynucleotide synthesis showing a second serial addition of overhanging oligonucleotide duplexes on a support (bead) with a universal anchor.

Referring to FIGS. 3-4, an exemplary method for multiplexed gene synthesis is shown. In FIG. 3, solid supports (e.g., beads) are prepared which have overhanging (offset) anchor stubs for each gene in the build (e.g., 100 different anchor stub types on each bead). The beads may be placed into a single well. In some embodiments, the method can comprise a M step multiplex synthesis. In some embodiments, in a first step, the first set of offset dimers {A1, B1, C1, D1 . . . N1}, designed to hybridize to the overhanging anchor stubs is then mixed into the well, and the offset dimers are allowed to anneal and to ligate to their appropriate anchor stubs. The beads are then washed. This cycle can then be repeated (see FIG. 4). In a second step in the M step multiplex synthesis, the second set of offset dimers, designed to hybridize to the first set of offset dimers, is now mixed into the well, and the offset dimers are allowed to anneal and to ligate to their appropriate first offset dimers. The beads are then washed. This cycle can be continued for M steps until the multiplexed polynucleotide assembly is complete.

In another embodiment (and referring to FIGS. 5-6), beads may be covered with a single type of offset overhanging anchor stub. Offset oligonucleotide dimers {A1, B1, C1, D1 . . . N1} may be designed to anchor to a common universal anchor stub (denoted UA in FIG. 6). In some embodiments, instead of beads, long (e.g., >200 bp) double-stranded polynucleotides with overhangs corresponding to the common anchor sequence may be used. In some embodiments, stem loop anchor oligonucleotides can be used (FIG. 7). In some embodiments, instead of a wash step the long double-stranded polynucleotide anchors may be separated from shorter double-stranded oligonucleotides. For example, the long double-stranded polynucleotide anchors may be separated from shorter double-stranded oligonucleotides by of size selection such as filter, gel or Solid Phase Reversible Immobilization (SPRI) beads.

In some embodiments, the 3' overhang can be generated using a nucleic acid hairpin structure or stem-loop oligonucleotide. The stem-loop structure may be formed by designing the oligonucleotides to have complementary sequences within its single-stranded sequence whereby the single-strand folds back upon itself to form a double-stranded stem and a single-stranded loop. In some embodiments, the double-stranded stem domain can have at least about 10 base pairs and the single stranded loop has at least 3, at least 5, at least 10, at least 20, at least 50 nucleotides. The stem can comprise an overhanging single-stranded region, i.e., the stem is a partial duplex. In some embodiments, the stem can comprise a 3' overhang. In an exemplary embodiment, the 3' overhang length of the stem-loop oligonucleotide is complementary to the 3' single-stranded overhang of the offset duplex to be added.

Figure 8:
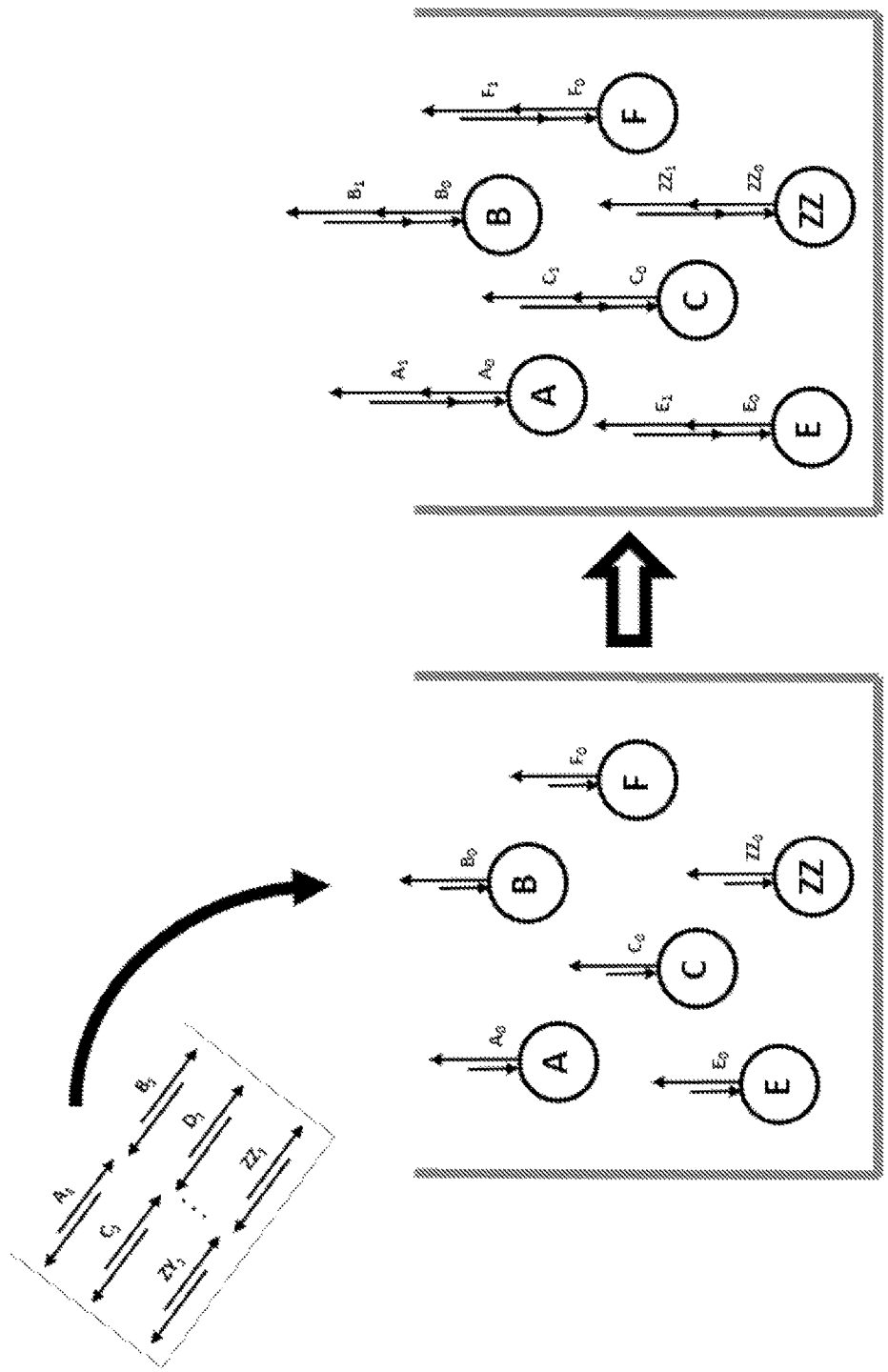
FIG. 8 illustrates a non-limiting exemplary method of serial multiplexed polynucleotide synthesis showing the first addition of overhanging oligonucleotide duplexes with one polynucleotide anchor species per bead.
Figure 9:
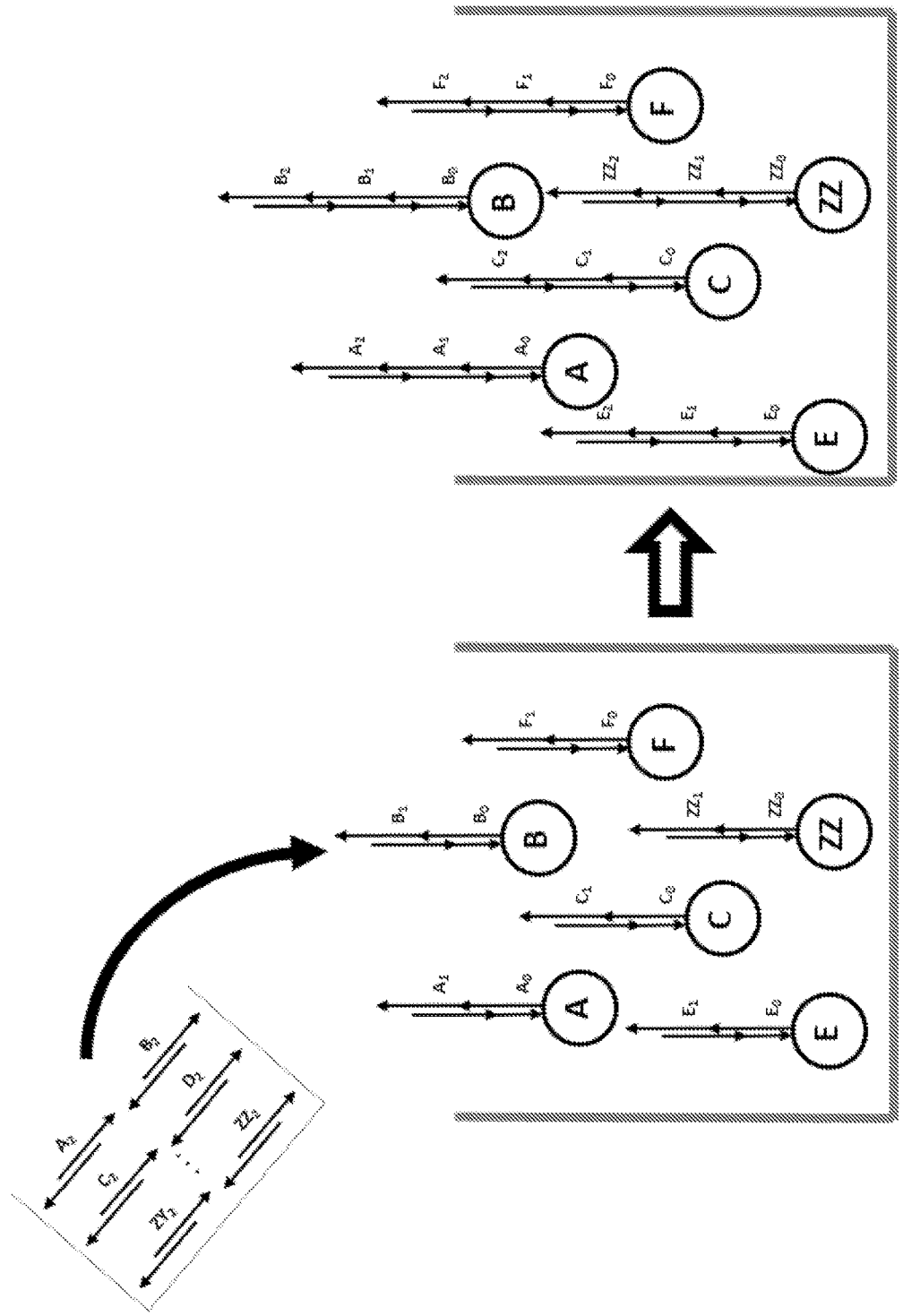
FIG. 9 illustrates a non-limiting exemplary method of hierarchical multiplexed polynucleotide synthesis showing the second addition of overhanging oligonucleotide duplexes with one polynucleotide anchor species per bead.

FIGS. 8 and 9 show exemplary Multiplexed Gene Synthesis with a single polynucleotide species per bead. Referring to FIG. 8, the beads for each gene in the build (e.g., 1000 different bead types for 1000 different genes) can be placed into a single well. The first set of offset dimers can then be mixed into the well, allowed to anneal to their appropriate bead stub and ligated. The beads can then be washed completing the first step in the M step multiplex synthesis. Referring to FIG. 9, the second set of offset dimers can now be mixed into the well, allowed to anneal to their appropriate first offset dimers and ligated. The beads can be then washed completing the second step in the M step multiplex synthesis. This cycle can be continued for M steps until the multiplexed gene assembly is complete.

Figure 10A:
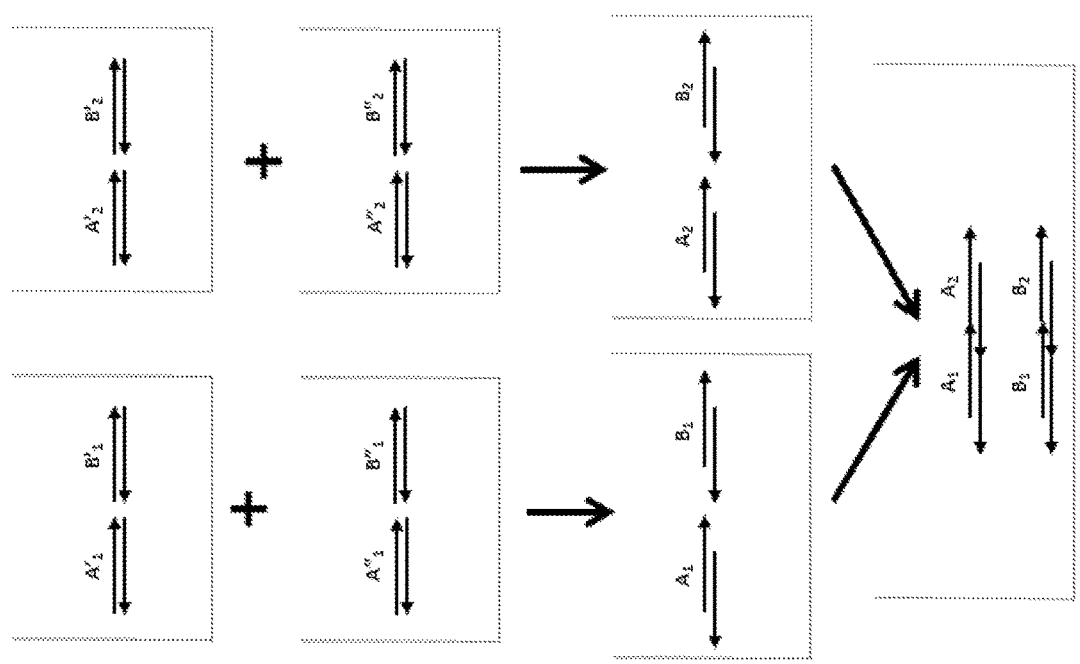
FIG. 10A illustrates a non-limiting exemplary method of forming offset dimers for multiplexed polynucleotide synthesis.
Figure 10B:
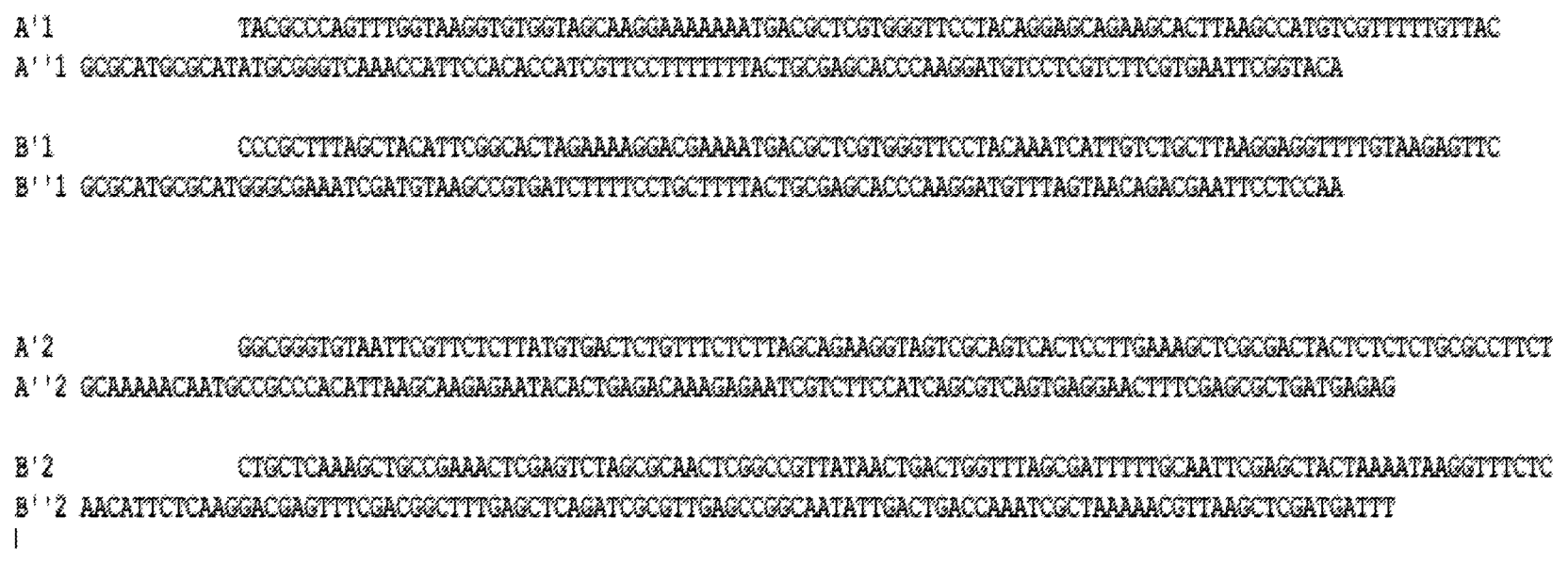

FIG. 10A is a schematic drawing of representing the melting and re-annealing of nucleic acid sequences to form MPS offset dimers having the correct sequence at their ends for hybridizing to each other to form longer polynucleotides. FIG. 10B shows exemplary sequences used in forming the MPS offset dimers A'1-A"1 (SEQ ID NO 1, SEQ ID NO 2), B'1-B"1 (SEQ ID NO 3, SEQ ID NO 4), A'2-A"2 (SEQ ID NO 5, SEQ ID NO 6) and B'2-B"2 (SEQ ID NO 7, SEQ ID NO 8).

Hierarchical Multiplexed Polynucleotide Synthesis

One should appreciate that a method for increasing the efficiency of construction of desired polynucleotides is to reduce the number of steps in the construction process. In some embodiments, the polynucleotides are synthesized using a hierarchical construction method, where multiple anchor arrays, after several rounds of transfer from construction arrays, may be used themselves as construction arrays in the following steps.

In some embodiments, to reduce the total number of processing steps required in sequential MPS, a process termed hierarchical MPS may be employed in which oligonucleotides can be assembled pairwise and hierarchically. As an example to construct N different polynucleotides each consisting of 8 oligonucleotides, the following 3 sets of hierarchical reactions can be carried out:

1] First Set of (4) Parallel Reactions:

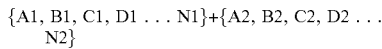

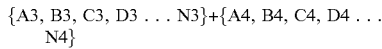

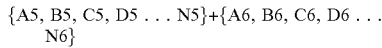

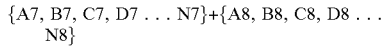

2] Second Set of (2) Parallel Reactions:

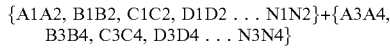

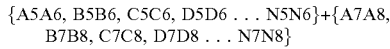

3] Third Reaction:

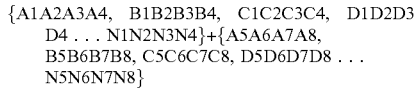

The above reactions can yield to N polynucleotides each of length 8 oligonucleotides. In general the number of hierarchical reactions is equal to $\log_2 [M]$, where M is the number of oligonucleotides per polynucleotide.

As with sequential MPS, each hybridization/ligation reaction only involves one junction at a time. Although the hierarchical MPS build does not include a wash step, it should be appropriate as long as the overlaps are sufficiently distinct across junctions, or the unligated material is in low enough concentration that the correct assembly dominates. The hierarchical approach has the advantage to reduce both the number of operations and the total process duration.

Both serial and hierarchical MPS can be suitable to long constructs (e.g., >1 Kb) since each step only involves one junction for each construct.

Figure 11:
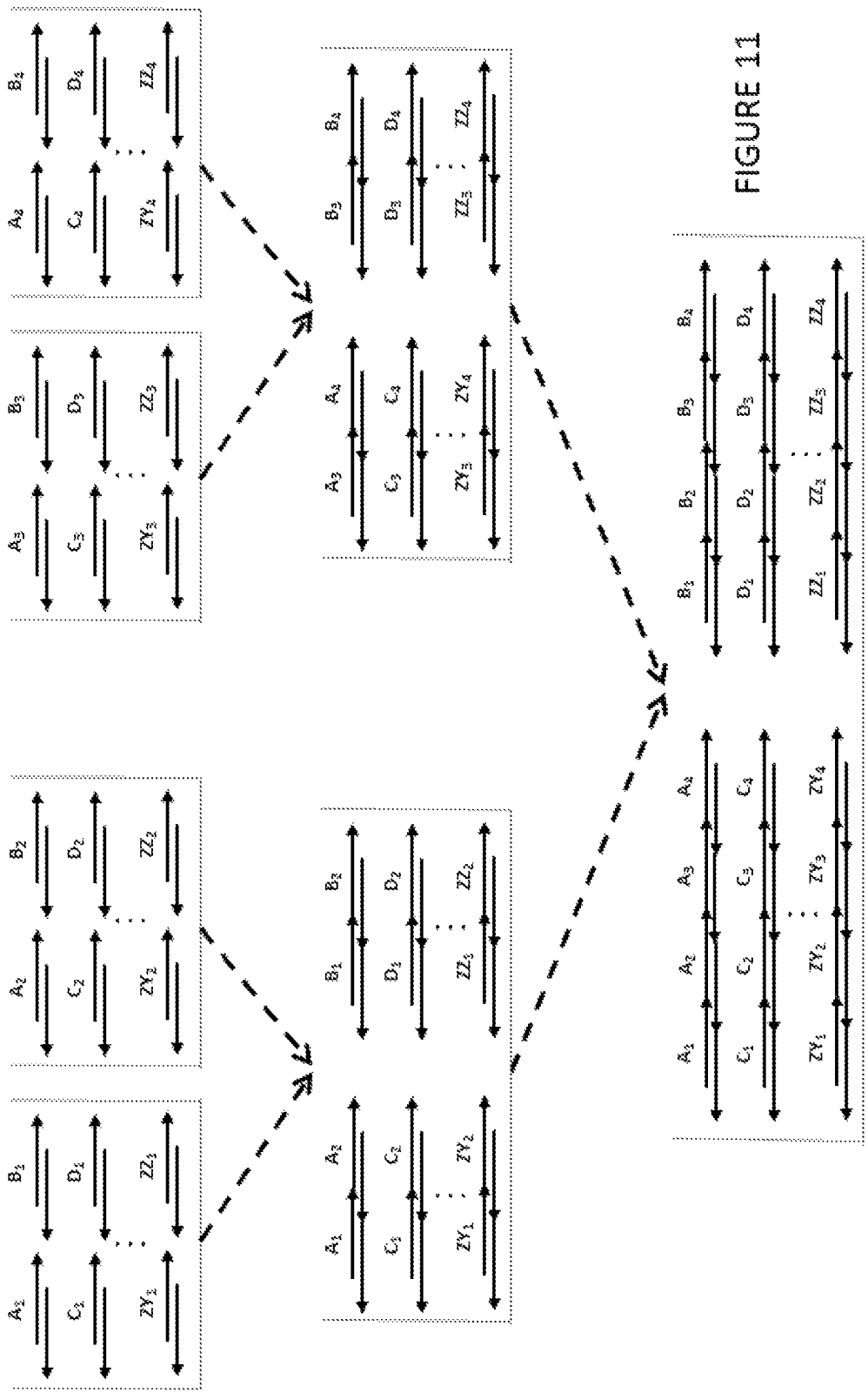
FIG. 11 illustrates a non-limiting exemplary method of hierarchical multiplexed polynucleotide synthesis.

FIG. 11 is a schematic of hierarchical MPS in which, in a first multiplex reaction, first offset dimers are hybridized and ligated to second offset dimers and third offset dimers are hybridized and ligated to fourth offset dimers such that:

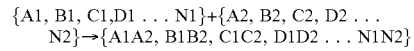

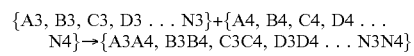

In a second multiplex reaction the two products from the above reaction are hybridized and ligated to yield the final product such that:

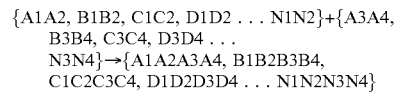

There are a total of 3N junctions in the example above. These junctions can be designed to be orthogonal, at least at each stage of hierarchy, so that the probability of off target hybridization and ligation can be kept low.

Parallel Multiplexed Polynucleotide Synthesis

In some embodiments, referred herein as parallel MPS, double-stranded overhanging oligonucleotides can be prepared which have sufficient coding space such that many junctions can uniquely come together and be ligated without a significant probability of mis-ligating to an off target junction. In an exemplary embodiment, parallel MPS may be used to assemble 20 constructs of 10 oligonucleotides each for a total of 200 junctions.

One of skill in the art would understand that one benefit of parallel MPS is that only a single reaction is required. The ultimate build size may be limited by terminating reactions and trapped states in which intermediate pairwise products, for example A1A2 and A2A3, can form. This can prevent the product A1A2A3 from forming. In order to overcome this problem, means for titrating the concentration of construction oligonucleotides are provided.

Figure 12:
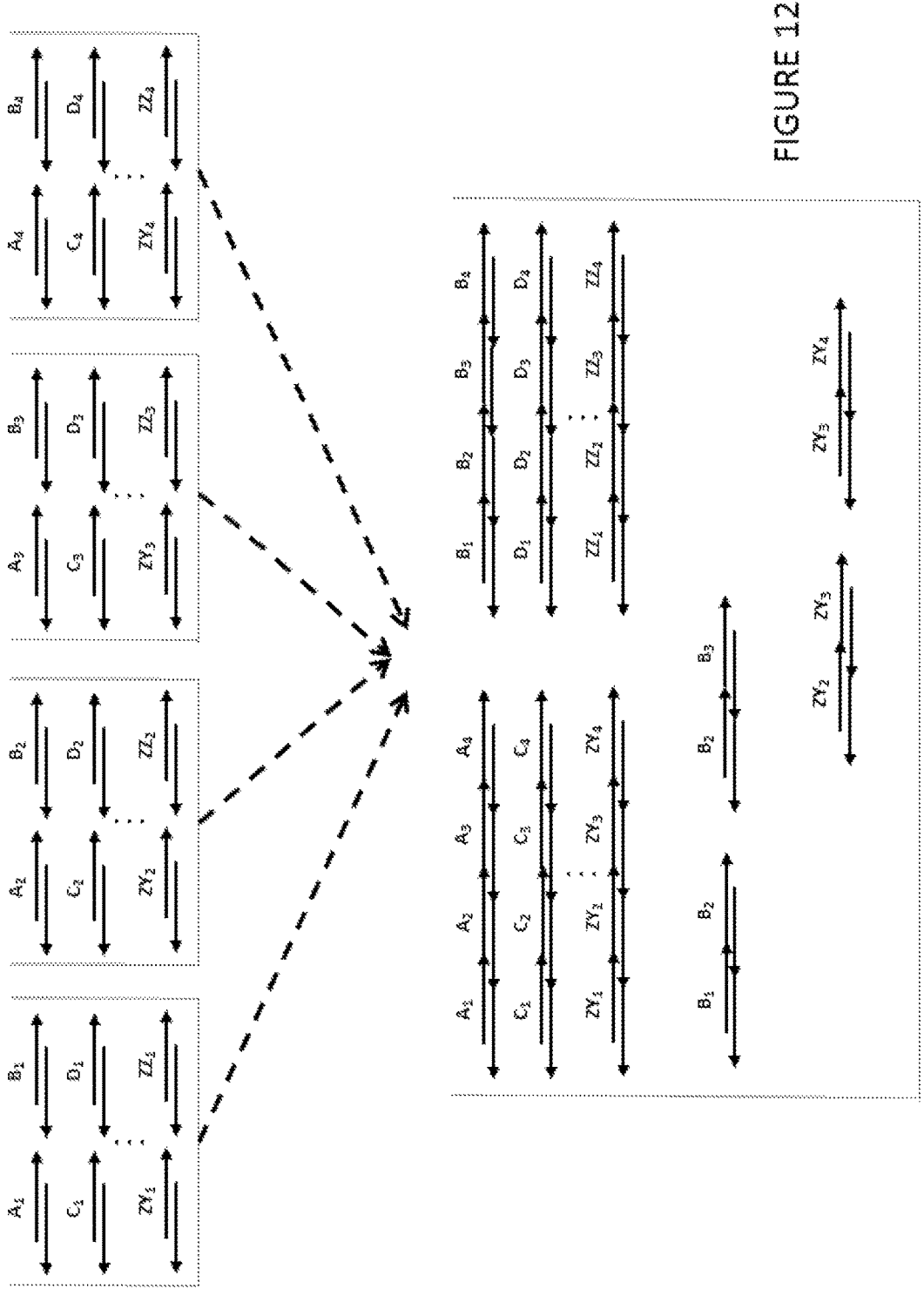
FIG. 12 illustrates a non-limiting exemplary method of parallel multiplexed polynucleotide synthesis.

FIG. 12 is a schematic of parallel MPS in which, in a single multiplex reaction, first, second, third and fourth offset dimers are hybridized to yield final product such that:

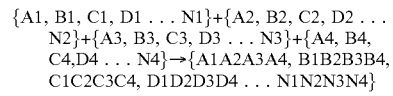

In the example shown above, there are a total of 3N junctions. These 3N junctions can be designed to be globally orthogonal to each other, so that the probability of off target hybridization and ligation can be kept low.

Figure 13A:
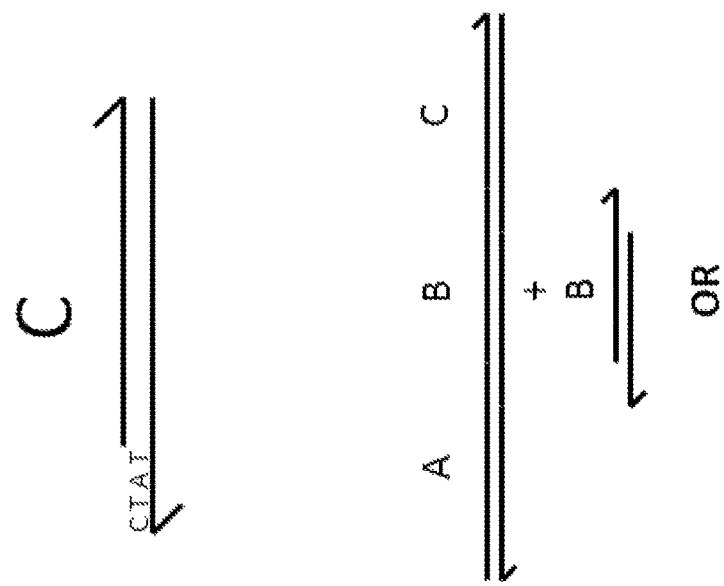
FIGS. 13A-13B illustrate a non-limiting exemplary method of terminating reactions within parallel multiplexed polynucleotide synthesis.
Figure 13B:
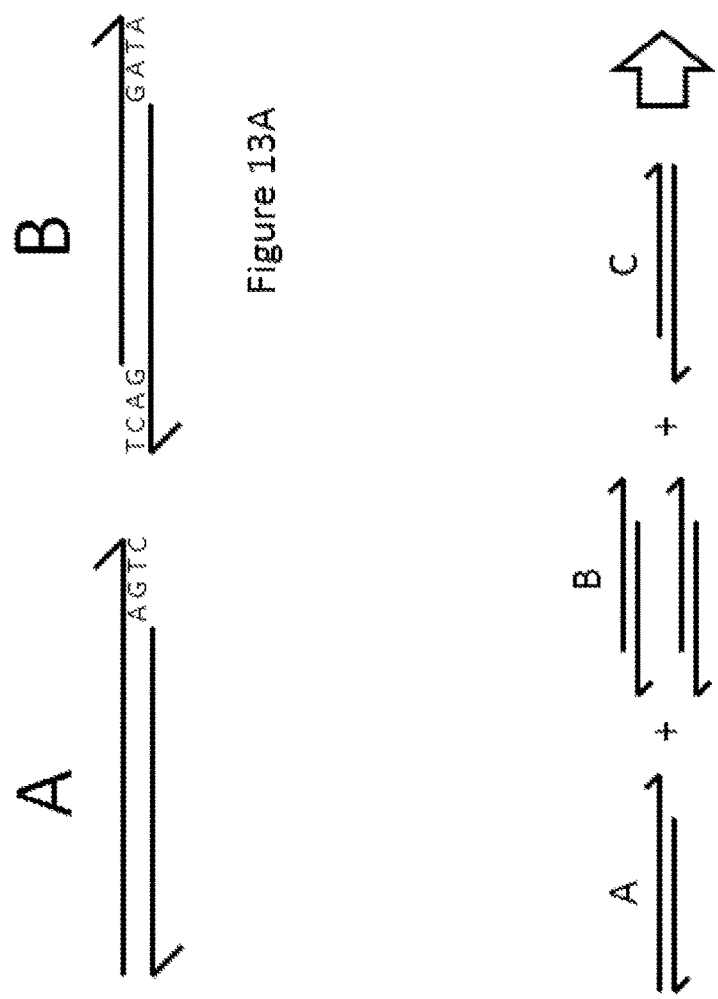

FIG. 13 illustrates the possibility of termination reactions with multi offset dimer assembly. FIG. 13A is a schematic representation of 3 offset dimers A, B, and C, which are designed to hybridize and ligate to a final product ABC. If there is an abundance of offset dimer B, then a trapped state or termination reaction may occur in which products AB and BC are formed, precluding the formation of desired product ABC (FIG. 13B).

Figure 14:
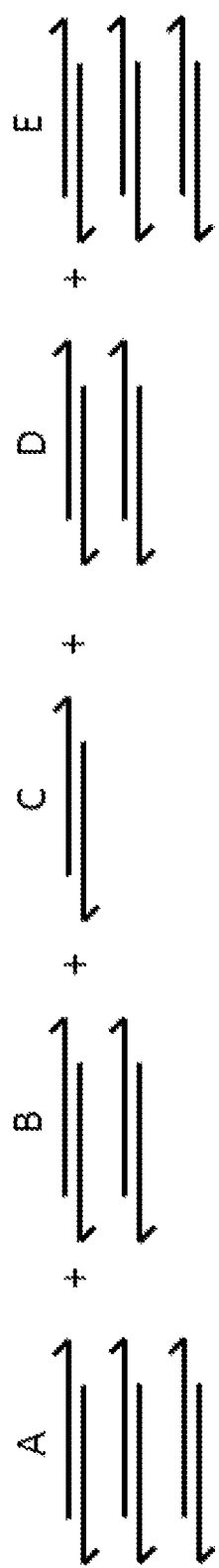
FIG. 14 illustrates a non-limiting exemplary method of parallel multiplexed polynucleotide synthesis using shaped concentration profiles of overhanging oligonucleotide duplexes to reduce terminating reactions.

FIG. 14 is a schematic representation of a first exemplary solution to the problem of termination reactions in multi offset dimer assembly and uses a tailored concave offset dimer concentration distribution (lower concentration for interior dimers). This distribution can reduce the formation of termination products.

Figure 15:
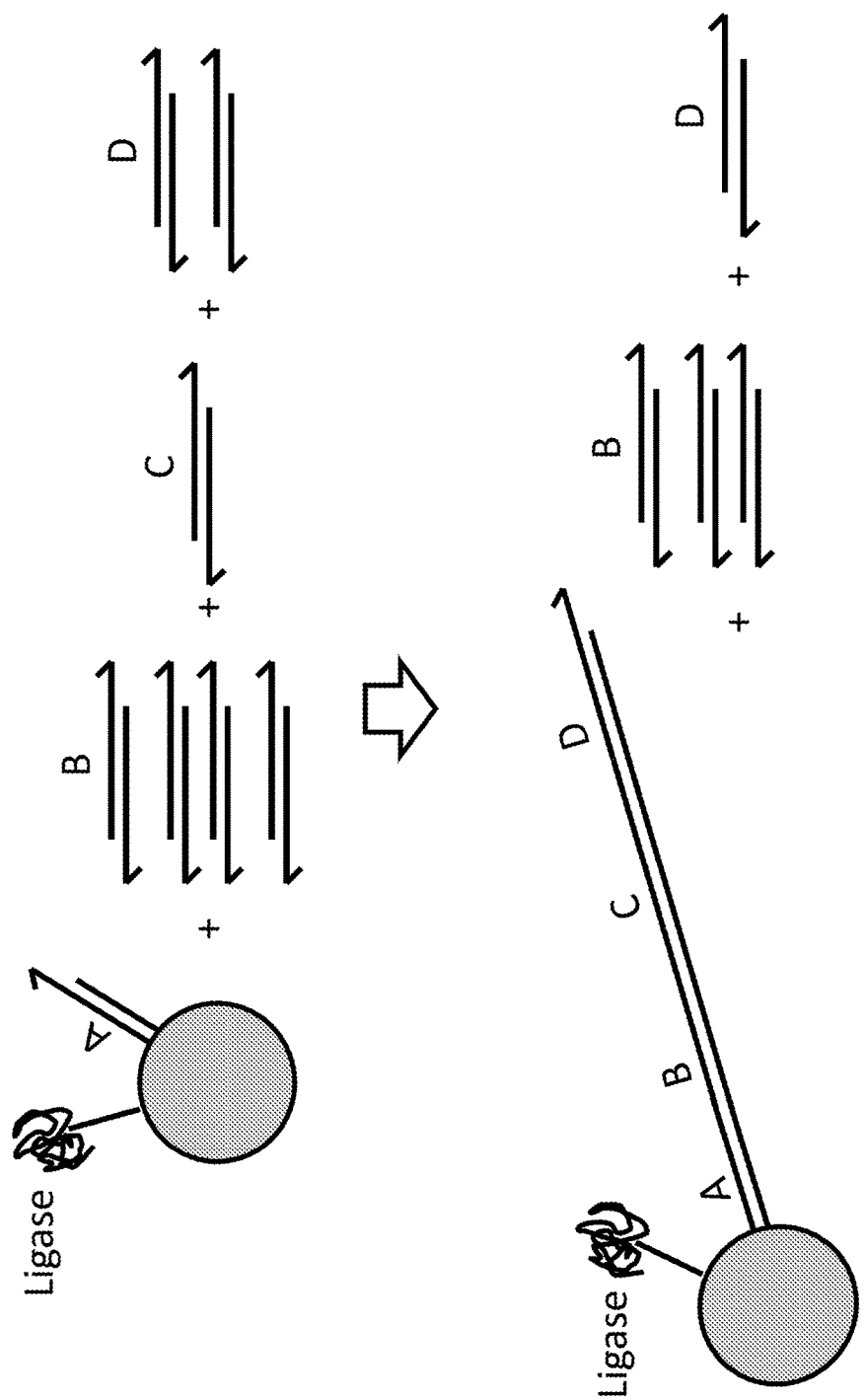
FIG. 15 illustrates a non-limiting exemplary method of parallel multiplexed polynucleotide synthesis using tethered ligase to reduce terminating reactions.

FIG. 15 is a schematic representation of a second exemplary solution to the problem of termination reactions in multi offset dimer assembly and uses a tethered ligase such that termination products are not formed in solution. Rather offset dimers can only be ligated in sequence on the bead surface. This method still constitutes parallel MPS since all of the offset dimers for a given polynucleotide may be introduced in parallel into solution.

FIG. 16 is a schematic representation of a third exemplary solution to the problem of termination reactions in multi offset dimer assembly and uses beads to capture quantitative numbers of each offset dimer thus titrating the number of each offset dimer and minimizing the probability of formation of termination products.

Sequence Analysis and Fragment Design and Selection

Aspects of the invention may include analyzing the sequence of a target nucleic acid and designing an assembly strategy based on the identification of regions, within the target nucleic acid sequence, that can be used to generate appropriate cohesive ends (e.g., single-stranded overhangs). These regions may be used to define the ends of nucleic acid fragments that can be assembled (e.g., in one reaction) to generate the target nucleic acid. The nucleic acid fragments can then be provided or made (e.g., in a multiplex assembly reaction). The nucleic acid fragments can be selected such that they have a relative uniform size for ease to handle (e.g., by purification).

According to some embodiments, the nucleic acid sequence can be designed and/or analyzed in a computer-assisted manner to generate a set of parsed double-stranded or single-stranded oligonucleotides. As used herein, the term "parsed" means that a sequence of target nucleic acid has been delineated, for example in a computer-assisted manner, such as to identify a series of adjacent oligonucleotide sequences. Adjacent oligonucleotides or nucleic acid fragments preferably overlap by an appropriate number of nucleotides to facilitate assembly according the methods of the invention. The oligonucleotide sequences can be individually synthesized and assembled using the methods of the invention.

In some embodiments, a target nucleic acid sequence may be analyzed to identify regions that contain at least one different nucleotide on one strand of the target nucleic acid. These regions may be used to generate cohesive ends. It should be appreciated that the length of a cohesive end can be sufficient to provide specificity. For example, cohesive ends may be long enough to have sufficiently different sequences (e.g., at least 1-base differences) to prevent or reduce mispairing between similar cohesive ends. However, the length of the cohesive ends can be not long enough to stabilize mispairs between similar cohesive sequences. In some embodiments, a length of about 3 to about 10 bases may be used. However, any suitable length may be selected for a region that is to be used to generate a cohesive overhang. The importance of specificity may depend on the number of different fragments that are being assembled simultaneously. Also, the appropriate length required to avoid stabilizing mispaired regions may depend on the conditions used for annealing different cohesive ends.

In some embodiments, alternating regions may be selected if they are separated by distances that define fragments with suitable lengths for the assembly design. In some embodiments, the alternating regions may be separated by about 100 to about 500 bases. In some embodiments, the alternating regions may be separated by about 100 bases, about 200 bases, about 300 bases, or about 500 bases. However, any suitable shorter or longer distance may be selected. For example, the cohesive regions may be separated by about 200 to about 1,000 bases. In some embodiments, the alternating regions may be separated by about 300 bases, about 400 bases, about 600 bases, about 700 bases, about 800 bases, about 900 bases, about 1000 bases. It should be appreciated that different patterns of alternating regions may be available depending on several factors (e.g., depending on the sequence of the target nucleic acid, the chosen length of the cohesive ends, and the desired fragment length). In some embodiments, if several options are available, the regions may be selected to maximize the sequence differences between different cohesive ends.

Selection of the cohesive regions defines the fragments that will be assembled to generate the target nucleic acid. Accordingly, the fragment size may be between about 100 and about 500 base pairs long, between about 200 and about 1,000 bases long, or shorter or longer depending on the target nucleic acid. In some embodiments, the fragment size may be about 100 bases, 200 bases, 300 bases, 400 bases, 500 bases, 600 bases, 700 bases, 800 bases, 900 bases, 1,000 bases long. The fragments may be generated or obtained using any suitable technique. In some embodiments, each fragment may be assembled (e.g., in a multiplex duplex assembly reaction) so that it is flanked by double-stranded regions that can be used to generate the cohesive single-stranded regions.

In some embodiments, methods are provided for enabling the assembly of a target polynucleotide based upon information of the sequence of the target nucleic acid. In some embodiments, a computer software can be used to parse the target sequence (e.g., $A_1$-$A_n$) breaking it down into a set of overlapping oligonucleotides ($A_1$, $A_2$, $A_3$, of specified length. Oligonucleotides $A_1$, $A_2$, $A_3$, can be synthesized from a chip or microarray.

Support

As used herein, the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials can include but are not limited to, paper, synthetic filters and the like. In such porous materials, the reaction may take place within the pores. The support can have any one of a number of shapes, such as pin, strip, plate, disk, rod, bends, cylindrical structure, particle, including bead, nanoparticle and the like. The support can have variable widths.

The support can be hydrophilic or capable of being rendered hydrophilic. The support can include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like; either used by themselves or in conjunction with other materials.

In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein, the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature can be chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

Arrays may be constructed, custom ordered or purchased from a commercial vendor (e.g., CombiMatrix, Agilent, Affymetrix, Nimblegen). Oligonucleotides are attached, spotted, immobilized, surface-bound, supported or synthesized on the discrete features of the surface or array. Oligonucleotides may be covalently attached to the surface or deposited on the surface. Various methods of construction are well known in the art, e.g., maskless array synthesizers, light directed methods utilizing masks, flow channel methods, spotting methods etc.

In other embodiments, a plurality of oligonucleotides may be synthesized or immobilized (e.g., attached) on multiple supports, such as beads. One example is a bead based synthesis method which is described, for example, in U.S. Pat. Nos. 5,770,358, 5,639,603, and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles. Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods known in the art. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

Single-Stranded Overhangs

In certain embodiments, the overlapping complementary regions between adjacent nucleic acid fragments are designed (or selected) to be sufficiently different to promote (e.g., thermodynamically favor) assembly of a unique alignment of nucleic acid fragments (e.g., a selected or designed alignment of fragments). Surprisingly, under proper ligation conditions, difference by as little as one nucleotide affords sufficient discrimination power between perfect match (100% complementary cohesive ends) and mismatch (less than 100% complementary cohesive ends). As such, 4-base overhangs can allow up to $(4^4+1)=257$ different fragments to be ligated with high specificity and fidelity.

It should be appreciated that overlapping regions of different lengths may be used. In some embodiments, longer cohesive ends may be used when higher numbers of nucleic acid fragments are being assembled. Longer cohesive ends may provide more flexibility to design or select sufficiently distinct sequences to discriminate between correct cohesive end annealing (e.g., involving cohesive ends designed to anneal to each other) and incorrect cohesive end annealing (e.g., between non-complementary cohesive ends).

To achieve such high fidelity assembly, one or more suitable ligases may be used. A ligase may be obtained from recombinant or natural sources. In some embodiments, T3 DNA ligase, T4 DNA ligase, T7 DNA ligase, and/or E. coli DNA Ligase may be used. These ligases may be used at relatively low temperature (e.g., room temperature) and particularly useful for relatively short overhangs (e.g., about 3, about 4, about 5, or about 6 base overhangs). In certain ligation reactions (e.g., 30 min incubation at room temperature), T7 DNA ligase can be more efficient for multi-way ligation than the other ligases. A heat-stable ligase may also be used, such as one or more of Tth DNA ligase; Pfu DNA ligase; Taq ligase, any other suitable heat-stable ligase, or any combination thereof.

In some embodiments, two or more pairs of complementary cohesive ends between different nucleic acid fragments may be designed or selected to have identical or similar sequences in order to promote the assembly of products containing a relatively random arrangement (and/or number) of the fragments that have similar or identical cohesive ends. This may be useful to generate libraries of nucleic acid products with different sequence arrangements and/or different copy numbers of certain internal sequence regions.

It should be noted that to ensure ligation specificity, the overhangs can be selected or designed to be unique for each ligation site; that is, each pair of complementary overhangs for two fragments designed to be adjacent in an assembled product should be unique and differ from any other pair of complementary overhangs by at least one nucleotide.

Other methods for generating cohesive ends can also be used. For example, a polymerase based method (e.g., T4 DNA polymerase) can be used to synthesize desirable cohesive ends. Regardless of the method of generating specific overhangs (e.g., complementary overhangs for nucleic acids designed to be adjacent in an assembled nucleic acid product), overhangs of different lengths may be designed and/or produced. In some embodiments, long single-stranded overhangs (3' or 5') may be used to promote specificity and/or efficient assembly. For example, a 3' or 5' single-stranded overhang may be longer than 8 bases long, e.g., 8-14, 14-20, 20-25, 25-50, 50-100, 100-500, or more bases long.

High Fidelity Assembly

According to aspects of the invention, a plurality of nucleic acid fragments may be assembled in a single procedure wherein the plurality of fragments is mixed together under conditions that promote covalent assembly of the fragments to generate a specific longer nucleic acid. According to aspects of the invention, a plurality of nucleic acid fragments may be covalently assembled in vitro using a ligase. In some embodiments, 5 or more (e.g., 10 or more, 15 or more, 15 to 20, 20 to 25, 25 to 30, 30 to 35, 35 to 40, 40 to 45, 45 to 50, 50 or more, etc.) different nucleic acid fragments may be assembled. However, it should be appreciated that any number of nucleic acids (e.g., 2, 3, 4, 5, 6, 7, 8, 9, 10, 11, 12, 13, 14, 15, 16, 17, 18, 19, 20, etc.) may be assembled using suitable assembly techniques. Each nucleic acid fragment being assembled may be between about 100 nucleotides long and about 1,000 nucleotides long (e.g., about 200, about 300, about 400, about 500, about 600, about 700, about 800, about 900). However, longer (e.g., about 2,500 or more nucleotides long, about 5,000 or more nucleotides long, about 7,500 or more nucleotides long, about 10,000 or more nucleotides long, etc.) or shorter nucleic acid fragments may be assembled using an assembly technique (e.g., shotgun assembly into a plasmid vector). It should be appreciated that the size of each nucleic acid fragment may be independent of the size of other nucleic acid fragments added to an assembly. However, in some embodiments, each nucleic acid fragment may be approximately the same size or length (e.g., between about 100 nucleotides long and about 400 nucleotides long). For example, the length of the oligonucleotides may have a median length of between about 100 nucleotides long and about 400 nucleotides long and vary from about, +/−1 nucleotides, +/−4 nucleotides, +/−10 nucleotides. It should be appreciated that the length of a double-stranded nucleic acid fragment may be indicated by the number of base pairs. As used herein, a nucleic acid fragment referred to as "x" nucleotides long corresponds to "x" base pairs in length when used in the context of a double-stranded nucleic acid fragment. In some embodiments, one or more nucleic acids being assembled in one reaction (e.g., 1-5, 5-10, 10-15, 15-20, etc.) may be codon-optimized and/or non-naturally occurring. In some embodiments, all of the nucleic acids being assembled in one reaction are codon-optimized and/or non-naturally occurring.

In some aspects of the invention, nucleic acid fragments being assembled are designed to have overlapping complementary sequences. In some embodiments, the nucleic acid fragments are double-stranded nucleic acid fragments with 3' and/or 5' single-stranded overhangs. These overhangs may be cohesive ends that can anneal to complementary cohesive ends on different nucleic acid fragments. According to aspects of the invention, the presence of complementary sequences (and particularly complementary cohesive ends) on two nucleic acid fragments promotes their covalent assembly. In some embodiments, a plurality of nucleic acid fragments with different overlapping complementary single-stranded cohesive ends is assembled and their order in the assembled nucleic acid product is determined by the identity of the cohesive ends on each fragment. For example, the nucleic acid fragments may be designed so that a first nucleic acid has a first cohesive end that is complementary to a first cohesive end of a second nucleic acid and a second cohesive end that is complementary to a first cohesive end of a third nucleic acid. A second cohesive end of the second nucleic acid may be complementary to a first cohesive end of a fourth nucleic acid. A second cohesive end of the third nucleic acid may be complementary a first cohesive end of a fifth nucleic acid. And so on through to the final nucleic acid. According to aspects of the invention, this technique may be used to generate a linear arrangement containing nucleic acid fragments assembled in a predetermined linear order (e.g., first, second, third, fourth, . . . , final).

In certain embodiments, the overlapping complementary regions between adjacent nucleic acid fragments are designed (or selected) to be sufficiently different to promote (e.g., thermodynamically favor) assembly of a unique alignment of nucleic acid fragments (e.g., a selected or designed alignment of fragments). Surprisingly, under proper ligation conditions, difference by as little as one nucleotide affords sufficient discrimination power between perfect match (100% complementary cohesive ends) and mismatch (less than 100% complementary cohesive ends). As such, 4-base overhangs can allow up to (4^4+1)=257 different fragments to be ligated with high specificity and fidelity.

It should be appreciated that overlapping regions of different lengths may be used. In some embodiments, longer cohesive ends may be used when higher numbers of nucleic acid fragments are being assembled. Longer cohesive ends may provide more flexibility to design or select sufficiently distinct sequences to discriminate between correct cohesive end annealing (e.g., involving cohesive ends designed to anneal to each other) and incorrect cohesive end annealing (e.g., between non-complementary cohesive ends).

To achieve such high fidelity assembly, one or more suitable ligases may be used. A ligase may be obtained from recombinant or natural sources. In some embodiments, T3 DNA ligase, T4 DNA ligase, T7 DNA ligase, and/or E. coli DNA Ligase may be used. These ligases may be used at relatively low temperature (e.g., room temperature) and particularly useful for relatively short overhangs (e.g., about 3, about 4, about 5, or about 6 base overhangs). In certain ligation reactions (e.g., 30 min incubation at room temperature), T7 DNA ligase can be more efficient for multi-way ligation than the other ligases. A heat-stable ligase may also be used, such as one or more of Tth DNA ligase; Pfu DNA ligase; Taq ligase, any other suitable heat-stable ligase, or any combination thereof.

In some embodiments, two or more pairs of complementary cohesive ends between different nucleic acid fragments may be designed or selected to have identical or similar sequences in order to promote the assembly of products containing a relatively random arrangement (and/or number) of the fragments that have similar or identical cohesive ends. This may be useful to generate libraries of nucleic acid products with different sequence arrangements and/or different copy numbers of certain internal sequence regions.

In some embodiments, the nucleic acid fragments are mixed and incubated with a ligase. It should be appreciated that incubation under conditions that promote specific annealing of the cohesive ends may increase the frequency of assembly (e.g., correct assembly). In some embodiments, the different cohesive ends are designed to have similar melting temperatures (e.g., within about 5° C. of each other) so that correct annealing of all of the fragments is promoted under the same conditions. Correct annealing may be promoted at a different temperature depending on the length of the cohesive ends that are used. In some embodiments, cohesive ends of between about 4 and about 30 nucleotides in length (e.g., cohesive ends of about 5, about 10, about 15, about 20, about 25, or about 30 nucleotides in length) may be used. Incubation temperatures may range from about 20° C. to about 50° C. (including, e.g., room temperature). However, higher or lower temperatures may be used. The length of the incubation may be optimized based on the length of the overhangs, the complexity of the overhangs, and the number of different nucleic acids (and therefore the number of different overhangs) that are mixed together. The incubation time also may depend on the annealing temperature and the presence or absence of other agents in the mixture. For example, a nucleic acid binding protein and/or a recombinase may be added (e.g., RecA, for example a heat stable RecA protein).

The resulting complex of nucleic acids may be subjected to a polymerase chain reaction, in the presence of a pair of target-sequence specific primers, to amplify and select for the correct ligation product (i.e., the target nucleic acid). Alternatively, the resulting complex of nucleic acids can be ligated into a suitable vector and transformed into a host cell for further colony screening.

Error Reduction

A preparation of an oligonucleotide designed to have a certain sequence may include oligonucleotide molecules having the designed sequence in addition to oligonucleotide molecules that contain errors (e.g., that differ from the designed sequence at least at one position). A sequence error may include one or more nucleotide deletions, additions, substitutions (e.g., transversion or transition), inversions, duplications, or any combination of two or more thereof. Errors may be generated during oligonucleotide synthesis. Template oligonucleotides can have inherent errors as they are generally chemically synthesized (e.g., deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wide-type sequence of a gene of interest). For example, a template oligonucleotide can contain an error which can be a mismatch, deletion, or insertion. In PCR synthesis, the error is retained in the synthesized oligonucleotide. Additional errors can be introduced during PCR reactions.

It should be appreciated that different synthetic techniques may be prone to different error profiles and frequencies. In some embodiments, error rates may vary from $\frac{1}{10}$ to $\frac{1}{200}$ errors per base depending on the synthesis protocol that is used. However, in some embodiments, lower error rates may be achieved. Also, the types of errors may depend on the synthetic techniques that are used. For example, in some embodiments chip-based oligonucleotide synthesis may result in relatively more deletions than column-based synthetic techniques.

Accordingly, methods for error correction are needed for high-fidelity oligonucleotide synthesis. In some embodiments, one or more oligonucleotide preparations may be subjected to an error reduction or error filtration process to remove (or reduce the number or the frequency of) error-containing oligonucleotides. Such process can be used to increase the number of error-free oligonucleotides in the oligonucleotide preparations. Methods for conducting error reduction or error filtration can include, for example, hybridization to a selection oligonucleotide, binding to a mismatch binding agent or to a mismatch binding protein or combinations thereof.

In some embodiments, error correction may be included at the end of the synthesis process to increase the relative population of synthesized oligonucleotides without deviation from the desired sequences. In some embodiments, error correction is included after amplification of the oligonucleotides. Yet in other embodiments, the positive and negative strands can be synthesized and error correction may be included after annealing of the positive and negative strands.

Such error correction may include direct sequencing and/or the application of error correction based on correcting enzymes, such as error correcting nucleases (e.g., CEL I, CELII), error correction based on MutS or MutS homologs binding or other mismatch binding proteins (see, e.g., International Application No. PCT/US2010/057405), other means of error correction as known in the art or any combination thereof. In an exemplary embodiment, CEL I and/or CELII may be added to the oligonucleotide duplexes in the fluid medium. CEL is a mismatch specific endonuclease that cleaves all types of mismatches such as single nucleotide polymorphisms, small insertions or deletions. Addition of the endonuclease results in the cleavage of the double-stranded oligonucleotides at the site or region of the mismatch.

It should be appreciated that synthetic oligonucleotides often have sequence errors. Accordingly, oligonucleotide preparations may be selected or screened to remove error-containing molecules as described in more detail herein. Error containing-oligonucleotides may be double-stranded homoduplexes having the error on both strands (i.e., incorrect complementary nucleotide(s), deletion(s), or addition(s) on both strands).

In some embodiments, mismatch recognition can be used to control the errors generated during oligonucleotide synthesis, gene assembly, and the construction of longer polynucleotides. After amplification of the support-bound nucleic acids, the nucleic acids duplexes can be first subjected to round(s) of melting and annealing (also referred herein as shuffling). In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands may reanneal with a complementary strand that contains no errors or that contains one or more different errors. As a result, error-containing strands may end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of oligonucleotides, the amount or frequency of error containing nucleic acids may be reduced. Any suitable method for removing heteroduplex molecules may be used, including chromatography, electrophoresis, selective binding of heteroduplex molecules, etc. In some embodiments, mismatch binding proteins that selectively (e.g., specifically) bind to heteroduplex nucleic acid molecules may be used. In some embodiments, the mismatch binding protein may be used on double-stranded oligonucleotides or polynucleotides in solution or immobilized onto a support.

By way of example, in a chain extension reaction (e.g., PCR) using primer (e.g., a universal amplification primer), the chemically synthesized oligonucleotides can serve as template strands for producing complementary strands. The resulting products can include error-free complementary strand (complementary to error-free template strand 11) and error-prone amplified complementary strand (complementary to error-prone template strand 12). Under melting conditions (e.g., an increased temperature at solid support or chip surface), the complementary strands are separated from the template strands. After shuffling, heteroduplex can be formed between an error-prone template strand and an error-free complementary strand. Heteroduplex can then be recognized and cleaved by a component (e.g., Surveyor endonuclease). Subsequent removal of cleaved, error-prone duplexes can result in an error-free chip surface.

In some embodiments, the oligonucleotides containing errors are removed using a MutS filtration process, for example, using MutS, a MutS homolog, or a combination thereof. It should be appreciated that error removal can make use of solid-phase MutS. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutS alpha) recognizes base mismatches and single nucleotide insertion/deletion loops, while the MSH2-MSH3 complex (also known as MutSbeta) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*), Taq MutS (from *Thermus aquaticus*), Apy MutS (from *Aquifex pyrophilus*), Tma MutS (from *Thermotoga maritima*), homologs thereof any other suitable MutS or any combination of two or more thereof.

It has been shown that MutS obtained from different species can have different affinity for a specific mismatch or for different mismatch. In some embodiments, a combination of different MutS having different affinities for different mismatch can be used.

In some embodiments, an enzyme complex using one or more repair proteins can be used. Example of repair proteins include, but are not limited to, MutS, for mismatch recognition, MutH, for introduction of a nick in the target strand, and MutL, for mediating the interactions between MutH and MutS, homologs thereof or any combinations thereof. In some embodiments, the mismatch binding protein complex is a MutHLS enzyme complex.

In some embodiments, a sliding clamp technique may be used for enriching error-free double stranded oligonucleotides. In some embodiments, MutS or homolog thereof can interact with a DNA clamp protein. Example of DNA clamp proteins include, but are not limited to, the bacterial sliding clamp protein DnaN, encoded by dnaN gene, which can function as a homodimer. In some embodiments, interaction of MutS protein, or homolog thereof, with a clamp protein can increase the effectiveness of MutS in binding mismatches.

In some embodiments, the oligonucleotides containing errors are removed using an enzyme from the S1 family of proteins, for example CEL1, CELII or a homolog thereof, such as RESI, or a combination thereof. Enzymes from the S1 family of proteins can recognize base mismatches, insertion and deletion loops. In some embodiments, such enzymes can bind preferentially to Holliday junctions after which the recognition site is cleaved, either through only one or both DNA strands. In some embodiments, a thermostable equivalent of a S1 protein may be used.

In some embodiments, the oligonucleotides containing errors are removed using a small molecule, chemical or inorganic material that binds to mismatched base sites. At the mismatched site, nucleotide bases are extra-helical and can be susceptible to chemical modification reactions. Materials such permanganate, hydroxylamine, lysine, and or pentaamine ruthenium can be employed in the chemical cleavage method to modify the mismatched thymine and cytosine respectively. The resulting modified DNA can then treated with piperidine to cause a cleavage at the abasic sites. In some embodiments, specificity of cleavage can be monitored using divalent salt.

Applications

Aspects of the invention may be useful for a range of applications involving the production and/or use of synthetic nucleic acids. As described herein, the invention provides methods for assembling synthetic nucleic acids with increased efficiency. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying suitable assembly techniques at one or more points to produce long nucleic acid molecules. For example, ligase-based assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agricultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e. using cell-free systems) or in vivo (i.e. expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexahistidine ($His^6$) Myc and HA, and other polypeptides with utility, such as $GFP_5$ GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids. In certain embodiments, synthetic nucleic acids may be provided as libraries for screening in research and development (e.g., to identify potential therapeutic proteins or peptides, to identify potential protein targets for drug development, etc.) In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

It should be appreciated that different acts or embodiments described herein may be performed independently and may be performed at different locations in the United States or outside the United States. For example, each of the acts of receiving an order for a target nucleic acid, analyzing a target nucleic acid sequence, designing one or more starting nucleic acids (e.g., oligonucleotides), synthesizing starting nucleic acid(s), purifying starting nucleic acid(s), assembling starting nucleic acid(s), isolating assembled nucleic acid(s), confirming the sequence of assembled nucleic acid(s), manipulating assembled nucleic acid(s) (e.g., amplifying, cloning, inserting into a host genome, etc.), and any other acts or any parts of these acts may be performed independently either at one location or at different sites within the United States or outside the United States. In some embodiments, an assembly procedure may involve a combination of acts that are performed at one site (in the United States or outside the United States) and acts that are performed at one or more remote sites (within the United States or outside the United States).

Automated Applications

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to International Patent Application Publication Number PCT/US12/052036 which is hereby incorporated by reference in its entirety. All publications, patents and sequence database entries mentioned herein are hereby incorporated by reference in their entirety as if each individual publication or patent was specifically and individually indicated to be incorporated by reference.

The invention claimed is:

1. A method of producing at least one target nucleic acid having a predefined sequence, the method comprising:
   a. providing a plurality of double-stranded anchor oligonucleotides having a first plurality of overhangs, wherein the anchor oligonucleotides are attached to a support;
   b. providing a plurality of double-stranded construction oligonucleotides having a second plurality of overhangs, wherein the second plurality of overhangs are designed to be complementary to the first plurality of overhangs;
   c. hybridizing and ligating the double-stranded anchor oligonucleotides with the double-stranded construction oligonucleotides; and
   d. optionally, repeating steps a)-c), thereby generating the at least one target nucleic acid.

2. The method of claim 1 wherein the first plurality of overhangs are designed to be relatively mutually orthogonal to each other.

3. The method of claim 1 wherein the second plurality of overhangs are designed to be relatively mutually orthogonal to each other.

4. The method of claim 1 wherein the support is solid.

5. The method of claim 4 wherein the support is a bead.

6. The method of claim 1 wherein the support is a stem loop polynucleotide.

7. The method of claim 1 wherein each of the plurality of the double-stranded anchor oligonucleotides is immobilized to the same support.

8. The method of claim 1 wherein each of the plurality of the double-stranded anchor oligonucleotides is immobilized to a different support.

9. The method of claim 1 wherein steps a)-d) are performed in a single reaction volume.

10. A method of producing at least one target nucleic acid having a predefined sequence, the method comprising:
    a. ligating a first plurality of double-stranded oligonucleotides having a first plurality of overhangs with a second plurality of double-stranded oligonucleotides having a second plurality of overhangs, wherein the first plurality of overhangs are designed to be complementary to the second plurality of overhangs, thereby producing a first set of polynucleotides; wherein the first plurality of overhangs are each designed to be relatively mutually orthogonal to each other; and wherein the second plurality of overhangs are each designed to be relatively mutually orthogonal to each other;
    b. ligating a third plurality of double-stranded oligonucleotides having a third plurality of overhangs with a fourth plurality of double-stranded oligonucleotides having a fourth plurality of overhangs, wherein the third plurality of overhangs are designed to be complementary to the fourth plurality of overhangs, thereby producing a second set of polynucleotides; wherein the third plurality of overhangs are each designed to be relatively mutually orthogonal to each other; and wherein the fourth plurality of overhangs are each designed to be relatively mutually orthogonal to each other; and
    c. ligating the first set of polynucleotides with the second set of polynucleotides, wherein the first set of polynucleotides and the second set of polynucleotides are designed to have complementary overhangs, thereby forming at least one target nucleic acid.

11. The method of claim 10 further comprising, repeating steps a)-c).

12. A method of producing at least one target nucleic acid having a predefined sequence, the method comprising:

ligating a first plurality of double-stranded oligonucleotides with a second plurality of double-stranded oligonucleotides at a 5' end of the second plurality of double-stranded oligonucleotides, and ligating the second plurality of double-stranded oligonucleotides with a third plurality of double-stranded oligonucleotides at a 3' end of the second plurality of double-stranded oligonucleotides, wherein the first plurality of double-stranded oligonucleotides have a first plurality of 3' overhangs, the second plurality of double-stranded oligonucleotides have a first plurality of 5' overhangs and a second plurality of 3' overhangs, and the third plurality of double-stranded oligonucleotides have a second plurality of 5' overhangs, wherein the first plurality of 3' overhangs are designed to be complementary to the first plurality of 5' overhangs, and the second plurality of 3' overhangs are designed to be complementary to the second plurality of 5' overhangs; wherein the first plurality of 3' overhangs are each designed to be relatively mutually orthogonal to each other; wherein the first plurality of 5' overhangs are each designed to be relatively mutually orthogonal to each other; wherein the second plurality of 3' overhangs are each designed to be relatively mutually orthogonal to each other; and wherein the second plurality of 5' overhangs are each designed to be relatively mutually orthogonal to each other;

thereby forming at least one target nucleic acid.

13. The method of claim 12 further comprising, repeating the ligating step.

14. The method of claim 2 wherein the second plurality of overhangs are designed to be relatively mutually orthogonal to each other.

* * * * *

SEQUENCE LISTING

<160> NUMBER OF SEQ ID NOS: 8

<210> SEQ ID NO 1
<211> LENGTH: 96
<212> TYPE: DNA
<213> ORGANISM: Artificial Sequence
<220> FEATURE:
<223> OTHER INFORMATION: Synthetic construct

<400> SEQUENCE: 1
tacgcccagt ttggtaaggt gtggtagcaa ggaaaaaaat gacgctcgtg ggttcctaca      60
ggagcagaag cacttaagcc atgtcgtttt tgttac                               96

<210> SEQ ID NO 2
<211> LENGTH: 96
<212> TYPE: DNA
<213> ORGANISM: Artificial Sequence
<220> FEATURE:
<223> OTHER INFORMATION: Synthetic construct

<400> SEQUENCE: 2
acatggctta agtgcttctg ctcctgtaag aacccacgag cgtcattttt ttccttgcta      60 ccacaccta ccaaactggg cgtatacgcg tacgcg                                96

<210> SEQ ID NO 3
<211> LENGTH: 96
<212> TYPE: DNA
<213> ORGANISM: Artificial Sequence
<220> FEATURE:
<223> OTHER INFORMATION: Synthetic construct

<400> SEQUENCE: 3
cccgctttag ctacattcgg cactagaaaa ggacgaaaat gacgctcgtg ggttcctaca      60
aatcattgtc tgcttaagga ggttttgtaa gagttc                               96

<210> SEQ ID NO 4
<211> LENGTH: 96
<212> TYPE: DNA
<213> ORGANISM: Artificial Sequence
<220> FEATURE:
<223> OTHER INFORMATION: Synthetic construct

<400> SEQUENCE: 4
aacctcctta agcagacaat gatttgtagg aacccacgag cgtcattttc gtccttttct      60
agtgccgaat gtagctaaag cgggtacgcg tacgcg                               96

<210> SEQ ID NO 5
<211> LENGTH: 100
<212> TYPE: DNA
<213> ORGANISM: Artificial Sequence
<220> FEATURE:
<223> OTHER INFORMATION: Synthetic construct

<400> SEQUENCE: 5
ggcgggtgta attcgttctc ttatgtgact ctgtttctct tagcagaagg tagtcgcagt      60
cactccttga aagctcgcga ctactctctc tgcgccttct                          100

<210> SEQ ID NO 6
<211> LENGTH: 100
<212> TYPE: DNA
<213> ORGANISM: Artificial Sequence
<220> FEATURE:
<223> OTHER INFORMATION: Synthetic construct -continued

```
<400> SEQUENCE: 6
gagagtagtc gcgagctttc aaggagtgac tgcgactacc ttctgctaag agaaacagag        60
tcacataaga gaacgaatta cacccgccgt aacaaaaacg                            100

<210> SEQ ID NO 7
<211> LENGTH: 100
<212> TYPE: DNA
<213> ORGANISM: Artificial Sequence
<220> FEATURE:
<223> OTHER INFORMATION: Synthetic construct

<400> SEQUENCE: 7
ctgctcaaag ctgccgaaac tcgagtctag cgcaactcgg ccgttataac tgactggttt        60
agcgattttt gcaattcgag ctactaaaat aaggtttctc                            100

<210> SEQ ID NO 8
<211> LENGTH: 100
<212> TYPE: DNA
<213> ORGANISM: Artificial Sequence
<220> FEATURE:
<223> OTHER INFORMATION: Synthetic construct

<400> SEQUENCE: 8
tttagtagct cgaattgcaa aaatcgctaa accagtcagt tataacggcc gagttgcgct        60
agactcgagt ttcggcagct ttgagcagga actcttacaa                            100
```